Figure 1A:
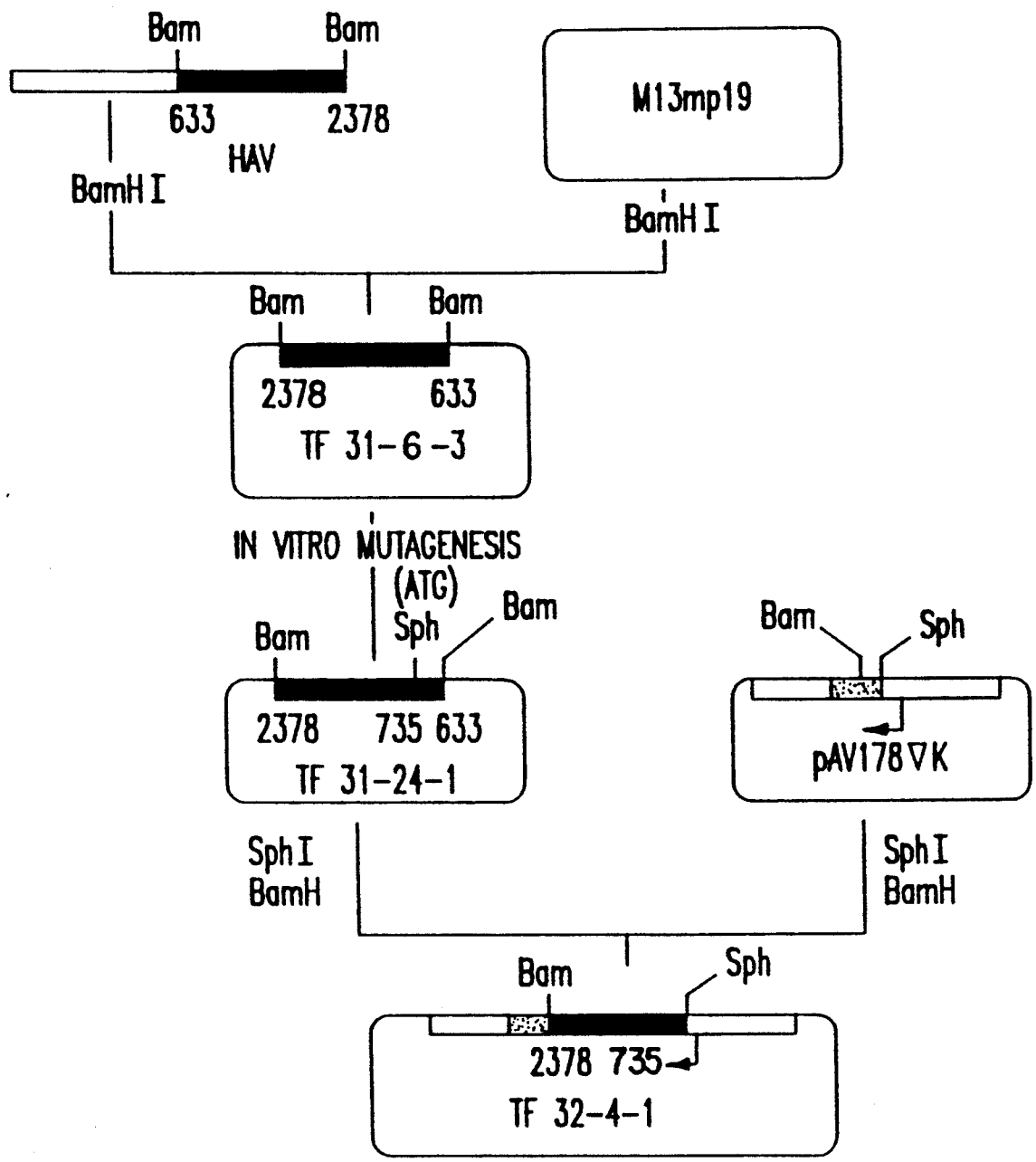

United States Patent [19]

McLinden et al.

[11] Patent Number: 5,294,548
[45] Date of Patent: Mar. 15, 1994

[54] RECOMBIANANT HEPATITIS A VIRUS

[75] Inventors: James H. McLinden, Mishawaka; Elliot D. Rosen, South Bend, both of Ind.; Patricia L. Winokur, Chevy Chase, Md.; Jack T. Stapleton, Iowa City, Iowa

[73] Assignees: American Biogenetic Sciences, Inc, Copiague, N.Y.; University of Iowa Research Foundation, Iowa City, Iowa

[21] Appl. No.: 725,178

[22] Filed: Jul. 3, 1991

Related U.S. Application Data

[63] Continuation-in-part of Ser. No. 502,900, Apr. 2, 1990, abandoned.

[51] Int. Cl.$^5$ .................. A61K 39/29; C12N 7/01; C12N 15/86
[52] U.S. Cl. .................. 435/235.1; 435/320.1; 530/350
[58] Field of Search .............. 435/240.2, 235.1, 320.1, 435/69.1; 536/27, 23.72

[56] References Cited

U.S. PATENT DOCUMENTS 4,745,051  5/1988  Smith et al. ..................... 435/69.1

FOREIGN PATENT DOCUMENTS

| | | | |
|---|---|---|---|
| 0127839 | 12/1984 | European Pat. Off. | C12N 15/00 |
| 0199480A2 | 10/1986 | European Pat. Off. | C12N 15/00 |
| 0276330A1 | 2/1988 | European Pat. Off. | C22N 15/00 |
| WO85/01517 | 4/1985 | PCT Int'l Appl. | C12N 15/00 |

OTHER PUBLICATIONS

Ticehurst et al., *Molecular Aspects of Picornavirus Infection and Detection*, 1989, pp. 27–50.
Ping et al., *J. Virology*, vol. 66, 1992, pp. 2208–2216.
Holmes et al., 1969, Science, 165:816–817.
Siegl et al., 1981, J. Gen. Virol. 57:331–341.
Locarnini et al., 1981, J. Virol. 37:216–225.
Miller, 1981, A Virus Vector for Genetic Engineering in Invertebrates, in Genetic Engineering in the Plant Sciences, Praeger Publishers, New York, pp. 203–224.
Coulepis et al., 1982, Intervirology 18:107–127.
Panicali et al., 1982, Proc. Natl. Acad. Sci. USA., 79:4927–4931.
Ticehurst et al., 1983, Proc. Natl. Acad. Sci. USA., 80:5885–5889.
Smith et al., 1983, J. Virol. 46:584–593.
Smith et al., 1983, Mol. Cell. Biol. 3:2156–2165.
Panicali et al., 1983, Proc. Natl. Acad. Sci. USA., 80:5364–5368.
Smith et al., 1983a, Proc. Natl. Acad. Sci. USA. 80:7155–7159.
Smith et al., 1983b, Nature, 302:490–495.
Lemon and Binn, 1983, J. Inf. Dis., 148:1033–1039.
Pennock et al., 1984, Mol. Cell Biol. 4:399–406.
Paoletti et al., 1984, Proc. Natl. Acad. Sci. USA. 81:193–197.
Smith et al., 1984, Science, 224:397–399.
Kieny et al., 1984, Nature, 312:163–166.
Wiktor et al., 1984, Proc. Natl. Acad. Sci. USA. 81:7194–7198.

(List continued on next page.)

*Primary Examiner*—Richard A. Schwartz
*Assistant Examiner*—James Ketter
*Attorney, Agent, or Firm*—Pennie & Edmonds

[57] ABSTRACT

The present invention is directed to genetically engineered expression systems which encode a recombinant Hepatitis A virus (HAV) proteins capable of forming capsid particles. By way of example baculovirus vectors were utilized in order to express recombinant HAV proteins. The recombinant baculoviruses of the invention are formed by replacing regions of the polyhedrin structural gene coding sequences with HAV DNA by recombinant DNA techniques. Additionally, the polyhedrin transcriptional initiation site is altered in these recombinant baculoviruses such that only HAV proteins and not polyhedrin protein sequences are expressed from the polyhedrin promoter. The recombinant HAV capsid particles produced in accordance with the present invention can be particularly useful as vaccines.

9 Claims, 23 Drawing Sheets

OTHER PUBLICATIONS

Smith et al., 1985, Proc. Natl. Acad. Sci. USA., 82:8404–8408.
Miyamoto et al., 1985, Mol. Cell Biol. 5:2860–2865.
Maeda et al., 1985, Nature, 315:592–594.
Yewdell et al., 1985, Nature, 279:246–248.
Mackett et al., 1985, Science, 227:433–435.
Kunkel, 1985, Proc. Natl. Acad. Sci. USA., 82:488–492.
Stepleton et al., 1985, Gastro. 89:637–642.
Provost et al., 1986, J. Med. Virol. 19:23–31.
Kuroda et al., 1986, EMBO J. 5:1359–1365.
Vallbrecht et al., 1986, Hepatology, 6:1308–1314.
Cohen et al., 1987, J. Virol. 61:50–59.
Cohen et al., 1987, Proc. Natl. Acad. Sci. USA., 84:2497–2501.
Walker et al., 1987, Nature, 328:345–348.
Ping et al., 1988, Proc. Natl. Acad. Sci. USA., 85:8281–8285.
Walker et al., 1988, Science, 240:64–66.
Lemon et al., 1989, Vaccines 89, Lavener, Ginsberg, Charock and Brown eds. Cold Spring Harbor Laboratory, pp. 423–426.
Emerson et al., 1989, ibid. 427–430.
Urakawa et al., 1989, J. Gen Virol., 70:1453–1463.
Luckow and Summers, 1989, Virology, 170:31–39.
Vallbracht et al., 1989, J. Inf. Dis., 160:209–217.
Baroudy et al., 1985, in Vaccines 85, Lerner, Chanock and Brown eds., Cold Spring Harbor Laboratory, pp. 249–254.
Cohen et al., 1987, J. Virol., 61:3035–3039.
Ticehurst et al., 1988, in Viral Hepatitis and Liver Disease, Alan R. Liss, Inc. pp. 33–35.
Cohen et al., 1988, ibid., pp. 67–69.
Karron et al., 1988, J. Inf. Disease, 157:338–345.
Ticehurst et al., 1989, in Molecular Aspects of Picornavirus Infection and Detection, Semler and Ehrenfeld, eds., Am. Soc. Microbiology, Washington, D.C., pp. 27–50.
Feng et al., 1989, Chinese J. Virol., 5:303–311 and Applicants informal translation thereof.
Mellen et al., *Biochemistry*, vol. 18, 1989, pp. 9881–9890.
Palmenberg et al., *J. Virol., vol. 32, 1979, pp. 770–778.*
Belsham et al., in *Vaccines 89,* 1989, Cold Spring Harbor Laboratory, pp. 445–448.
Jewell et al., *J. Virol.,* vol. 64, 1990, pp. 1388–1393.

FIG.8

| H | BV | r1 | r2 | r3 | r4 | r5 |

43 —

29 —

18 —

FIG. 13a

RECOMBIANANT HEPATITIS A VIRUS

CROSS REFERENCE TO RELATED APPLICATION

This is a continuation-in-part application of U.S. patent application Ser. No. 07/502,900, filed on Apr. 2, 1990, now abandoned.

TABLE OF CONTENTS

1. Field of Invention
2. Background of the Invention
   2.1. Hepatitis A Virus
   2.2. Recombinant DNA Techniques and Virus Expression Vectors
3. Summary of the Invention
4. Description of the Figures
5. Detailed Description of the Invention
   5.1. Cloning and Expression of Recombinant Hepatitis A Virus Polyprotein
   5.2. Construction of Expression Vectors Containing the HAV Coding Sequence
   5.3 Identification of Transfectants or Transformants Expressing the HAV Gene Product and Isolation of HAV
   5.4. Identification and Purification of the Expressed Gene Produce
   5.5. Determination of the Immunopotency of the Recombinant Product
   5.6. Formulation of Vaccine
      5.6.1. Capsid or Pentamer Vaccine Formulation
      5.6.2. Subunit Vaccine Formulations
      5.6.3. Viral Vaccine Formulations
6. Example: Expression of Recombinant HAV in a Baculovirus System
   6.1. Materials and Methods
      6.1.1. Construction of Recombinant Plasmids
      6.1.2. Preparation of Recombinant Baculoviruses
      6.1.3. Isolation of Recombinant Hepatitis A Virus Capsids
      6.1.4. protein Immunoblot (Western Blot) Analysis
   6.2. Results
Example: Expression of Recombinant HAV in a Vaccinia Virus System
   7.1. Materials & Methods
      7.1.1. Viruses
      7.1.2. Cells
      7.1.3. Transformation of Human B Cells
      7.1.4. Plasmid DNA
      7.1.5. Oligonucleotide Directed Mutagenesis
      7.1.6. Transfection and Isolation of Recombinant Vaccinia
      7.1.7. Polypeptide Analysis
      7.1.8. Animals Studies
      7.1.9. Radioimmunofocus Inhibition Assay
      7.1.10. Sera
   7.2. Results
      7.2.1. Construction of Plasmid and Virus Recombinants
      7.2.2. Expression of the HAV Structural Genes
      7.2.3. Murine Antibody Immune Response to HAV Epitopes
      7.2.4. Cytotoxic T Cell Response to HAV Epitopes
8. Example: Processing of the Recombinant HAV P1 Precursor Protein in Vaccinia Virus and in Baculovirus Expression Systems
9. Example: Isolation of Recombinant Hepatitis A Virus Capsids or Pentamers
10. Example: Evaluation of Hepatitis A Virus Particles Expressed by Recombinant Vaccinia Viruses
11. Deposit of Microorganisms

FIELD OF INVENTION

The present invention is directed to genetically engineered expression systems that encode recombinant Hepatitis A virus (HAV) proteins capable of forming capsid particles. The invention is also directed to genetically engineered expression systems that encode HAV epitopes that are antigenic and/or capable of eliciting an immune response.

The invention is demonstrated by way of examples in which baculovirus vectors or vaccinia virus vectors were utilized in order to express recombinant HAV proteins. The recombinant baculoviruses of the invention are formed by replacing regions of the polyhedrin structural gene coding sequences with HAV cDNA by recombinant DNA techniques. Additionally, the polyhedrin transcriptional initiation site is altered in these recombinant baculoviruses such that only HAV proteins and not polyhedrin protein sequences are expressed from the polyhedrin promoter. Recombinant vaccinia virus constructs were made that expressed the HAV polyprotein as well as segments of the HAV polyprotein under the control of the vaccinia P7.5 promoter and the $E.$ $coli$ $T_7$ phage polymerase promoter.

The HAV polyprotein expressed by recombinant baculoviruses and vaccinia viruses is processed into capsid proteins which assemble into virus-like particles. These recombinant HAV capsid particles produced in accordance with the present invention can be particularly useful in vaccine formulations.

2. BACKGROUND OF THE INVENTION

2.1. Hepatitis A Virus

Type A Hepatitis which accounts for approximately 40% of the cases of viral Hepatitis is caused by the Hepatitis A virus (HAV). The host range of HAV is limited to man, apes and several species of New World monkeys (Holmes et al., 1969, Science, 165: 816-817). The virus is spread primarily through fecal and oral contamination.

HAV is an ideal candidate for vaccine development. There is only one serotype and there is little antigenic variation between strains. In addition, immune serum globulin is effective in preventing HAV infection, suggesting the induction of a proper humoral response can be protective. While inactivated and attenuated HAV vaccines have produced protection in primate models (Provost et al., 1986, J. Med. Virol., 19: 23-31), the economy of protection and the risks associated with retained virulence have prevented the use of these strategies to produce commercial HAV vaccines.

The development of HAV epitopic or subunit vaccines has not been highly successful. Ping et al., 1985, Proc. Natl. Acad. Sci. U.S.A., 85: 8281-8285 "Characterization of the Immunodominant Antigenic Site of Hepatitis A Virus", Lemon et al., 1989, Vaccines 89 Cold Spring Harbor, pp. 423-426; Lavener, Charock and Brown, eds., "Identification of the Hepatitis-A Virus Genes Involved in Adaptation to Tissue-culture Growth and Attenuation", in Vaccines 89 Cold Spring Harbor. Although one can produce antibodies (Abs) to denatured proteins, they generally do not neutralize the virus suggesting that major neutralizing epitopes of intact HAV polypeptides may be discontinuous.

The Hepatitis A virus is a 27 nm non-enveloped plus stranded RNA containing member of the enterovirus genus of the picornavirus family (Coulepis et al., 1982, *Intervirology*, 18: 107–127). The genome of HAV is approximately 7500 nucleotides packaged in a nonenveloped icosahedral capsid and encodes a polyprotein of 2,227 amino acids (Cohen et al., 1987, *J. Virol.*, 61: 50–59). HAV RNA is infectious in cell culture and translation of the RNA yields a polyprotein that is processed to produce a variety of viral structural proteins and enzymes (Locarnini et al., 1981, *J. Virol.*, 37: 216–228; Siegl et al., 1981, *J. Gen. Virol.*, 57: 331–341). The structural proteins include, VP1, VP2, VP3 and possibly VP4, which compose the capsid. In addition, the polyprotein includes proteases, which are presumably involved in the processing of the polyprotein into constituent proteins.

The partial analysis of the sequence of a cDNA clone representing at least 99% of the genome of HAV was described (Ticehurst et al., 1983, *Proc. Natl. Acad. Sci. U.S.A.*, 80: 5885–5889). More recently, the complete nucleotide sequence of an attenuated cell cultureadapted hepatitis A virus cDNA was compared to the cDNA of wild type HAV (Cohen et al., 1987, *Proc. Natl. Acad. Sci. U.S.A.*, 84: 2497–2501; Cohen et al., 1987, *J. Virol.*, 61: 50–59). This full-length cDNA copy of HAV was transcribed and the RNA transfected into monkey kidney cells yields only low levels of HAV (Cohen et al., 1987, *J. Virol.*, 61:50–59).

2.2. Recombinant DNA Techniques and Virus Expression Vectors

Baculoviruses are useful as recombinant DNA vector systems since they are double stranded DNA replicating units into which can be inserted a large amount of foreign DNA (20 megadaltons) and which provide at least one strong promoter (polyhedrin), which controls a gene with nonessential function for propagation in cell culture, which is available for replacement or insertion into by foreign DNA (Miller, L. K., 1981, A Virus Vector for Genetic Engineering in Invertebrates, In Genetic Engineering in the Plant Sciences, Praegen Publishers, New York, pp. 203–224; Vlak, J. M. and Rohrmann, G. F., 1985 The Nature of Polyhedrin, In Viral Insecticides for Biological Control, Academic Press, pp. 489–542). A method for the production of recombinant proteins using a baculovirus system has been described (Pennock et al., 1984, *Mol. Cell. Biol.*, 4: 399; Smith et al., 1983, *J. Virol.*, 46: 584).

Several foreign proteins have been successfully expressed using baculovirus expression systems. Human interleukin 2 (Smith et al., 1985, *Proc. Natl. Acad. Sci. U.S.A.*, 82: 8404–8408), human c-myc (Miyamoto et al., 1985, *Mol. Cell. Biol.*, 5: 2860–2865), bacterial beta-galactosidase (Pennock et al., 1984, *Mol. Cell. Biol.*, 4: 399–406), influenza virus haemagglutinin (Kuroda et al., 1986, *EMBO* 5: 1359–1365), and human beta-interferon (Smith et al., 1983, *Mol. Cell. Biol.*, 3: 2156–2165) have all been expressed in insect cells under the control of the polyhedrin promoter in recombinant AcNPV expression vectors. Human alpha-interferon has been expressed in silkworms by ligation to the polyhedrin promoter of BmNPV (Maeda et al., 1985, *Nature*, (London) 315: 592–594). Smith and Summers (European Patent No. 0 127 839, Dec. 12, 1984) propose a method for producing recombinant baculovirus expression vectors, and report the use of recombinant AcNPV vectors to express human beta-interferon and human interleukin 2, under the control of the polyhedrin promoter. Recently, non-infectious poliovirus particles were synthesized in insect cells by a recombinant baculovirus expression vector containing the complete coding region of the P3/Leon/37 strain of poliovirus type 3 (Urakawa et al., 1989, *J. Gen. Virol.*, 70: 1453–1463).

Recently, higher yields of recombinant proteins expressed in a baculovirus vector resulted when the polyhedrin ATG start codon was altered, such that translation initiated at a downstream ATG codon (Luckow and Summers, 1989, *Virology*, 170: 31–39).

Recently, recombinant vaccinia virus has been used successfully to express foreign genes such as herpes simplex virus thymidine kinase, glycoprotein D (Panicali et al., 1982, *Proc. Natl. Acad. Sci. U.S.A.*, 79: 4927–4931; Paoletti et al., 1984, *Proc. Natl. Acad. Sci. U.S.A.*, 81: 193–197), influenza virus hemagglutinin, influenza virus nucleoprotein (Panicali et al., 1983, *Proc. Natl. Acad. Sci. U.S.A.*, 80: 5364–5368; Smith et al., 1983a, *Proc. Natl. Acad. Sci. U.S.A.*, 80: 7155–7159; Yewdell et al., 1985, *Nature*, 279: 246–248), Hepatitis B virus surface antigen (Smith et al., 1983b, *Nature*, 302: 490–495; Paoletti et al. 1984) *Plasmodium knowlesi* sporozoite antigen (Smith et al., 1984, *Science*, 224: 397–399), rabies virus glycoprotein (Kieny et al., 1984, *Nature*, 312: 163–166, Wiktor et al., 1984, *Proc. Natl. Acad. Sci. U.S.A.*, 81: 7194–7198) and vesicular stomatitis virus G and N proteins (Mackett et al., 1985, *Science*, 227: 433–435). These vaccinia recombinant viruses were able to induce both humoral and cell-mediated immune responses as well as to protect the infected host against disease when challenged with live virus. Thus, there is potential for the application of vaccinia virus recombinants as live virus vaccines against both human and animal infectious agents. However to date, no one has successfully expressed an HAV polypeptide in the vaccinia virus expression vector.

3. SUMMARY OF THE INVENTION

The present invention is directed to recombinant expression systems that are capable of producing non-infectious HAV capsid particles that provide protection from wild type HAV infection in vaccinated individuals. The invention is also directed to genetically engineered expression systems which encode HAV epitopes that are antigenic and/or capable of eliciting an immune response. By way of example, the present invention describes recombinant baculoviruses and vaccinia viruses containing the coding region of HAV expressing non-infectious but immunogenic HAV capsid particles that are useful as vaccine candidates. Vaccinia recombinants containing HAV epitopes, VP1, VP3 are also described.

4. DESCRIPTION OF THE FIGURES

FIG. 1A. Construction of vector TF 32-4-1 containing an epitope of HAV consisting of nucleotide positions 735–2378 base pairs of the HAV cDNA. Site-directed mutagenesis was used to create an SphI site (GCATGC) such that the ATG of the restriction site corresponds to the initiation methionine (ATG) at nucleotide position 735 of the HAV genome.

Figure 1B:
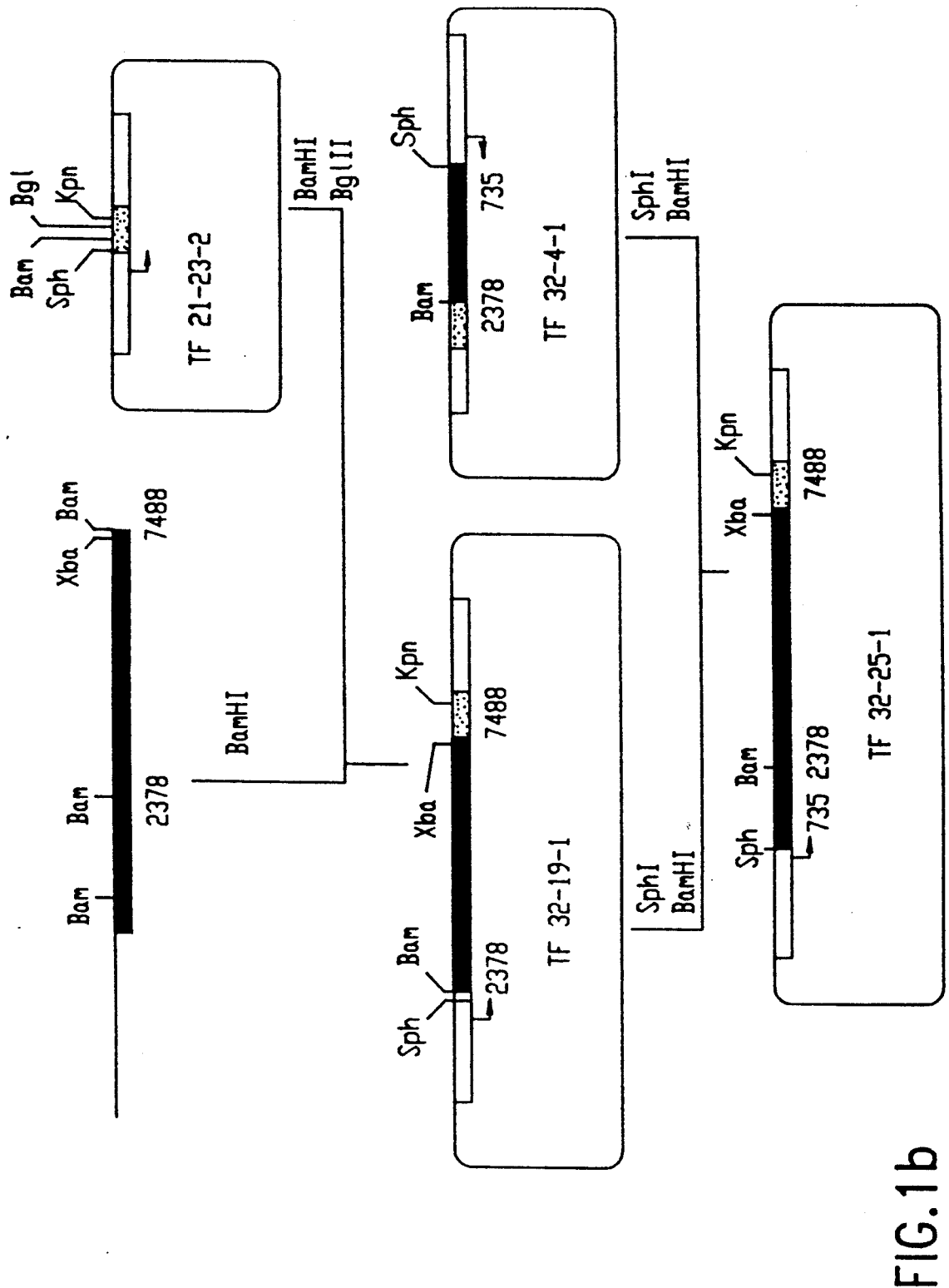

FIG. 1B. Construction of vector TF 32-25-1 in which an epitope of HAV consisting of nucleotide positions 735–2378 base pairs is fused to the remainder of the HAV polyprotein gene (2379–7488 base pairs). The HAV polyprotein gene (nucleotides 735-7488) was cloned into an SphI site at nucleotide position +1 adjacent to the polyhedrin promoter in a baculovirus vector.

Figure 2A:
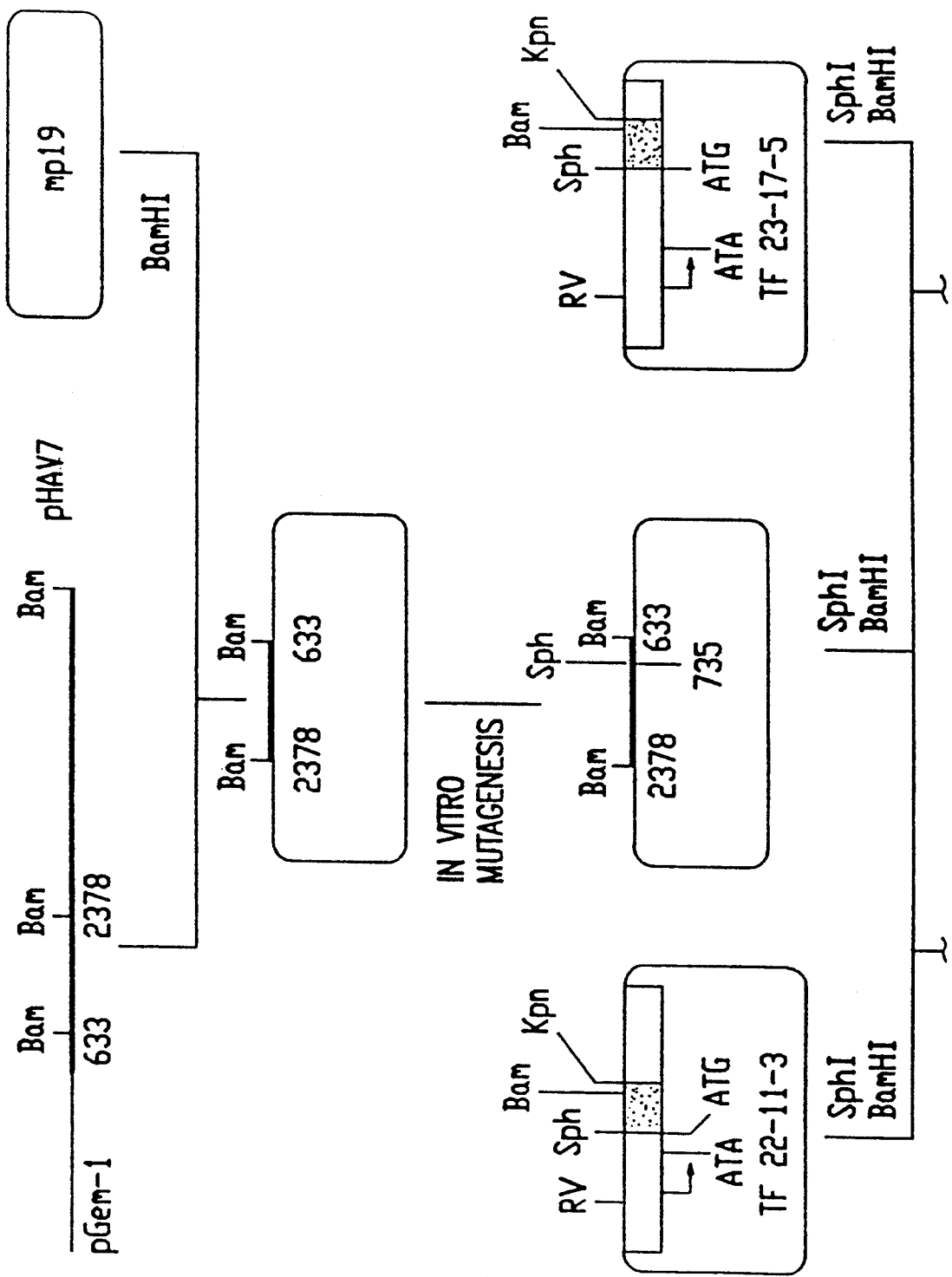
Figure 2B:
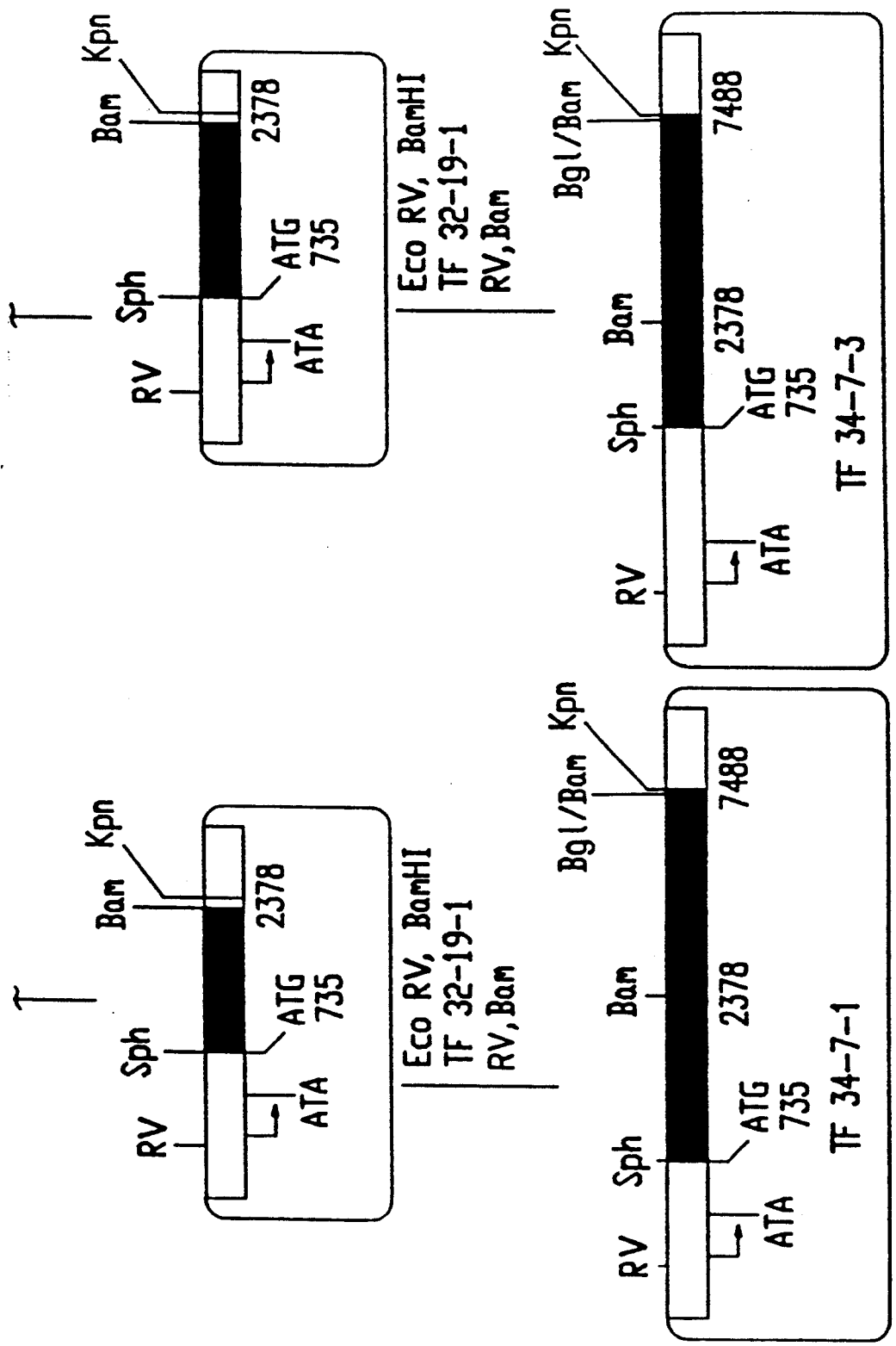

FIG. 2. Construction of vectors TF 34-7-1 and TF 34-7-3 in which the epitope of the HAV polypeptide gene cloned into a baculovirus vector in which the original ATG, translational start site of the polyhedrin sequence is altered and an ATG is introduced downstream in the polyhedrin coding sequence.

Figure 3A:
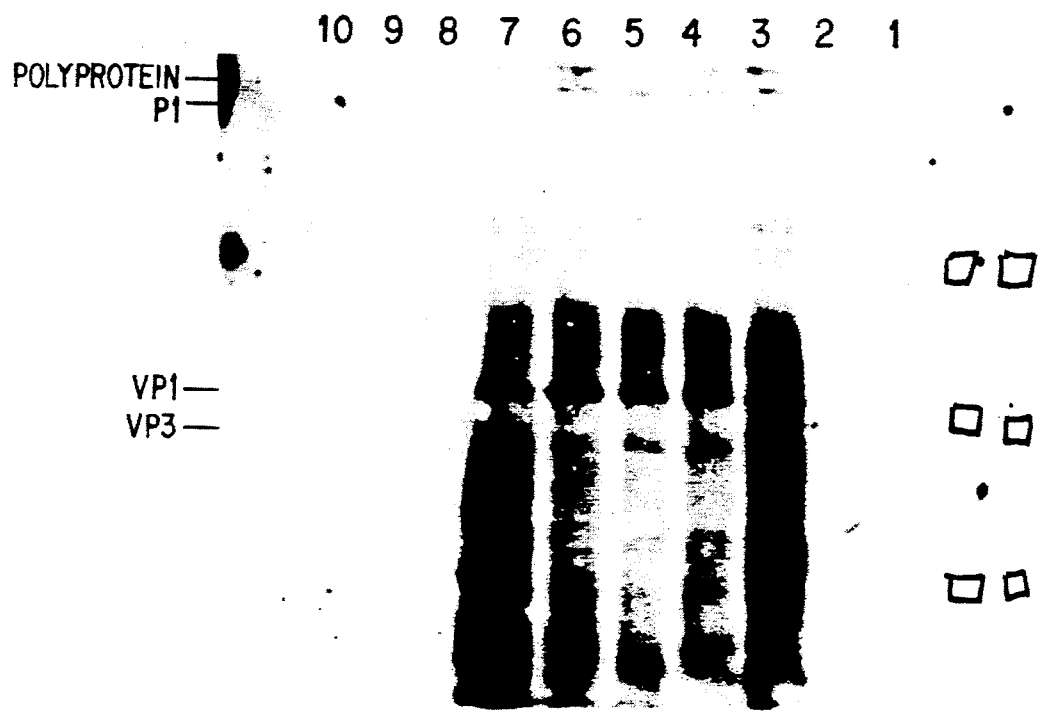
Figure 3B:
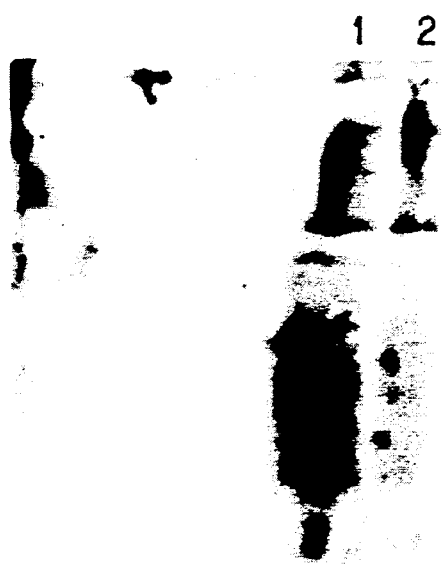

FIGS. 3A and 3B. Western blot analysis of insect cell extracts infected with recombinant viruses containing the HAV polyprotein cDNA sequence that were electrophoresed on SDS polyacrylamide gels, transferred to nitrocellulose paper and probed with anti-HAV VP1 antibody.

FIG. 3A. Lane 2, HAV; Lane 3, 414.2A1; Lane 4, 414. 3A1; Lane 5, 414.4A1; Lane 6, 414.1A1; Lane 7, 419.3A1; Lane 8, 419; Lane 9, 418. FIG. 3B. Lane 1, 419.1A1; Lane 2, 419.3A1.

Figure 4:
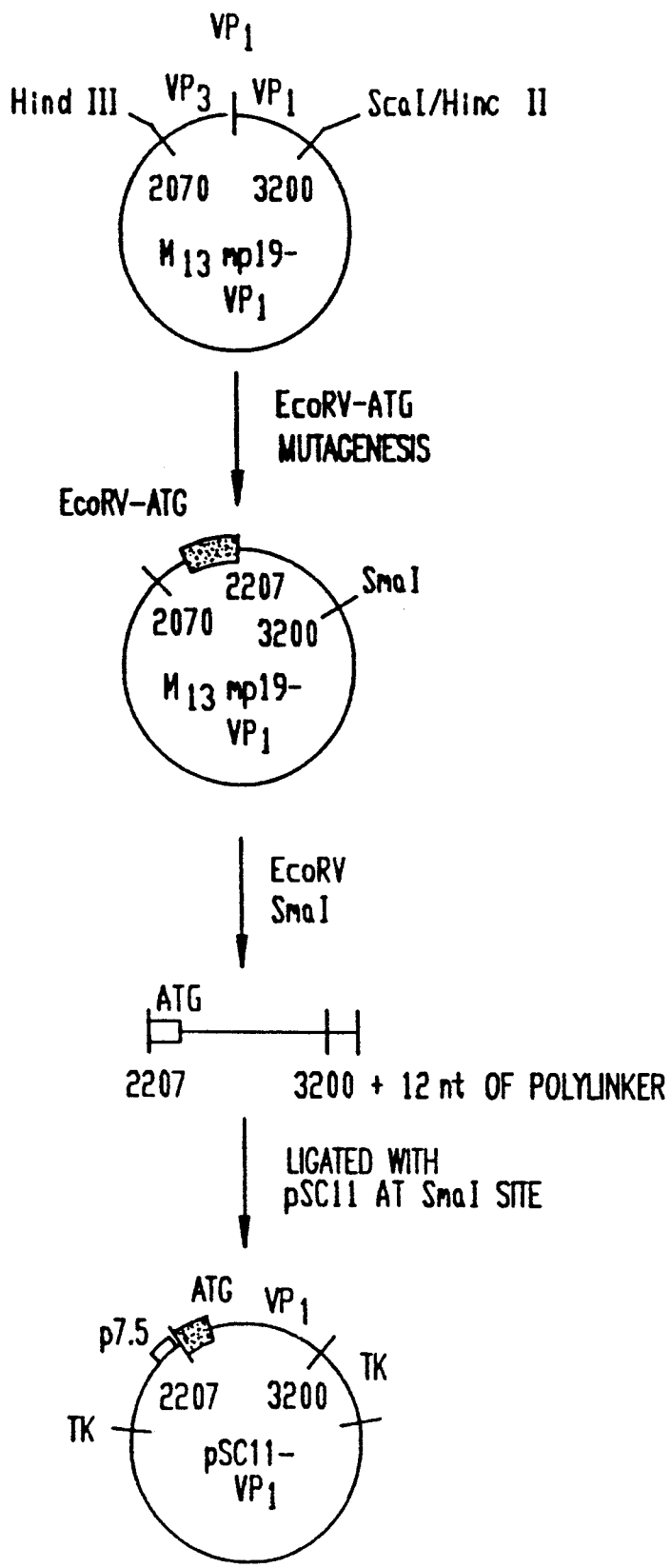

FIG. 4. Construction of vector HAV VP1 in which the epitope of HAV consisting of nucleotide positions 2207-3200 of the HAV cDNA are cloned into a vaccinia virus vector downstream of a p7.5 promoter. Oligonucleotide directed mutagenesis was used to insert new EcoRV restriction sites followed by an ATG in frame with the HAV coding sequence.

Figure 5:
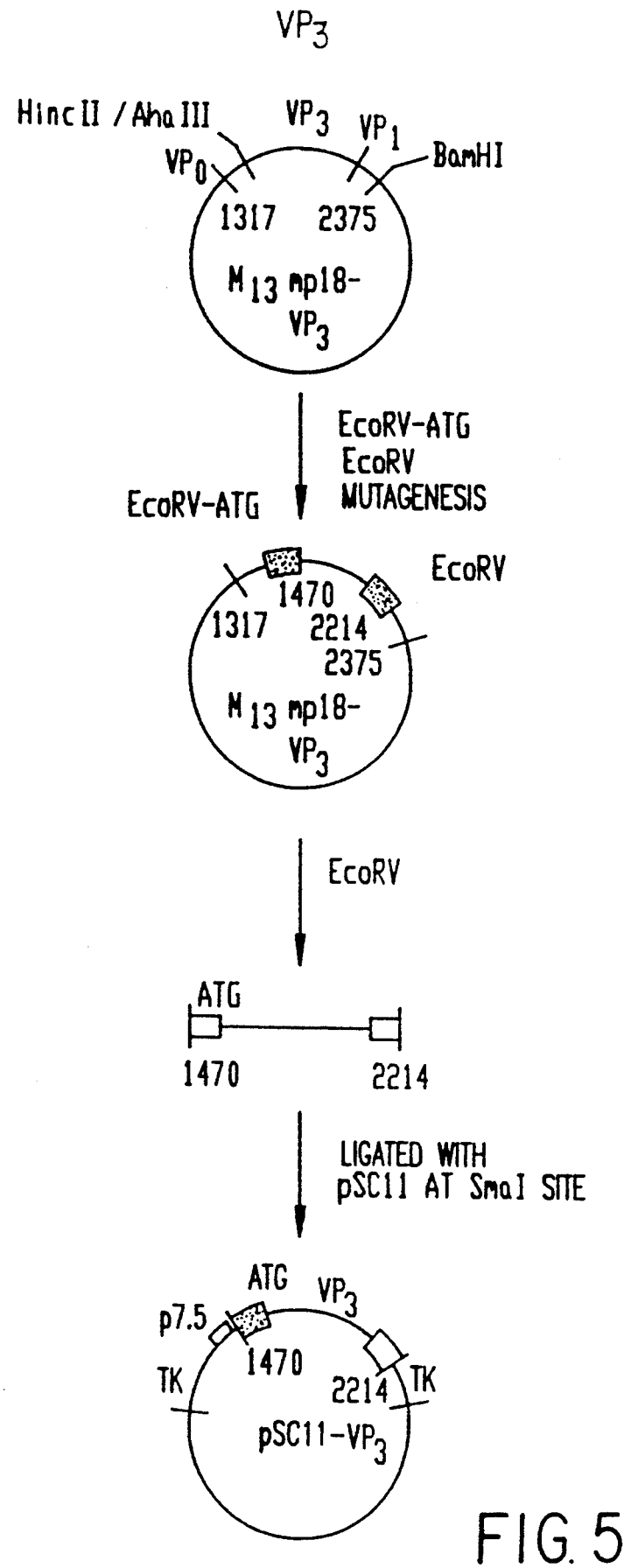

FIG. 5. Construction of vector HAV VP3 in which the VP3 epitope of HAV consisting of nucleotide positions 1470-2214 of the HAV cDNA is cloned into a vaccinia virus vector downstream of a p7.5 promoter. Oligonucleotide directed mutagenesis was used to insert new EcoRV restriction sites followed by an ATG in frame with the HAV coding sequence.

Figure 6:
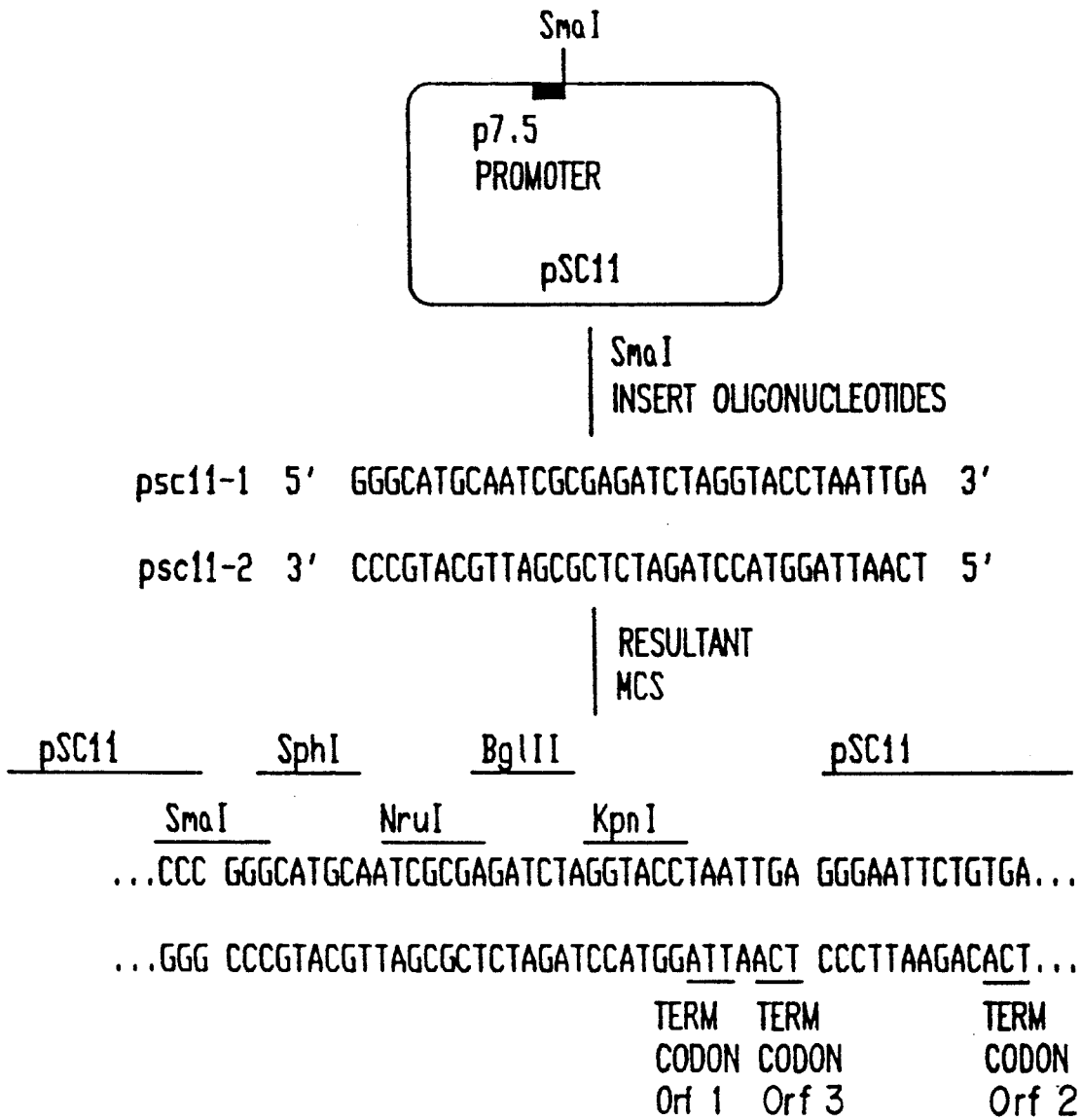

FIG. 6. Construction of vector PSC 11-J in which a multiple cloning site containing the following convenient restriction sites; (Sma I, Sph I, Nru I, Bgl II/ and Kpn I) along with termination codons in all three reading frames were cloned into the vaccinia virus vector PSC11 at the Sma I site downstream of the p7.5 promoter.

Figure 7:
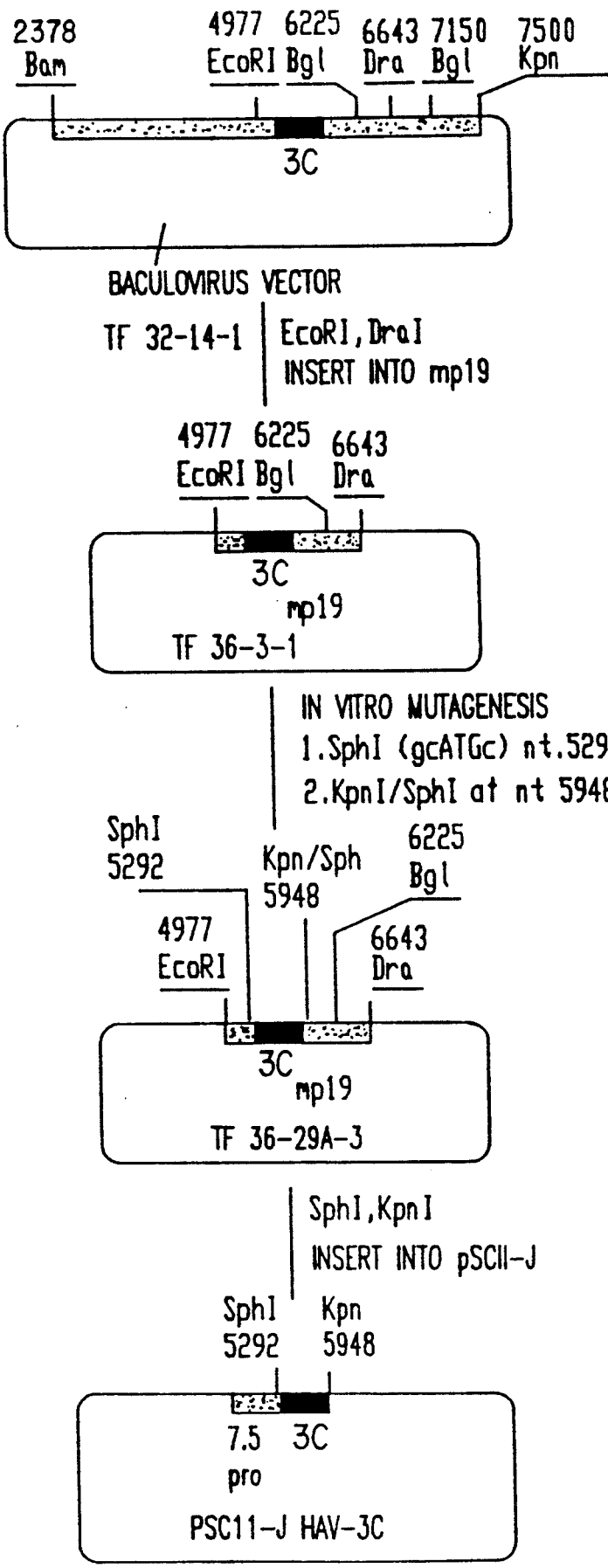

FIG. 7. Construction of vector PSC 11-J HAV-3C in which the protease gene of HAV consisting of nucleotide positions 5292-5948 of the HAV cDNA is cloned into a vaccinia virus vector.

Figure 8:
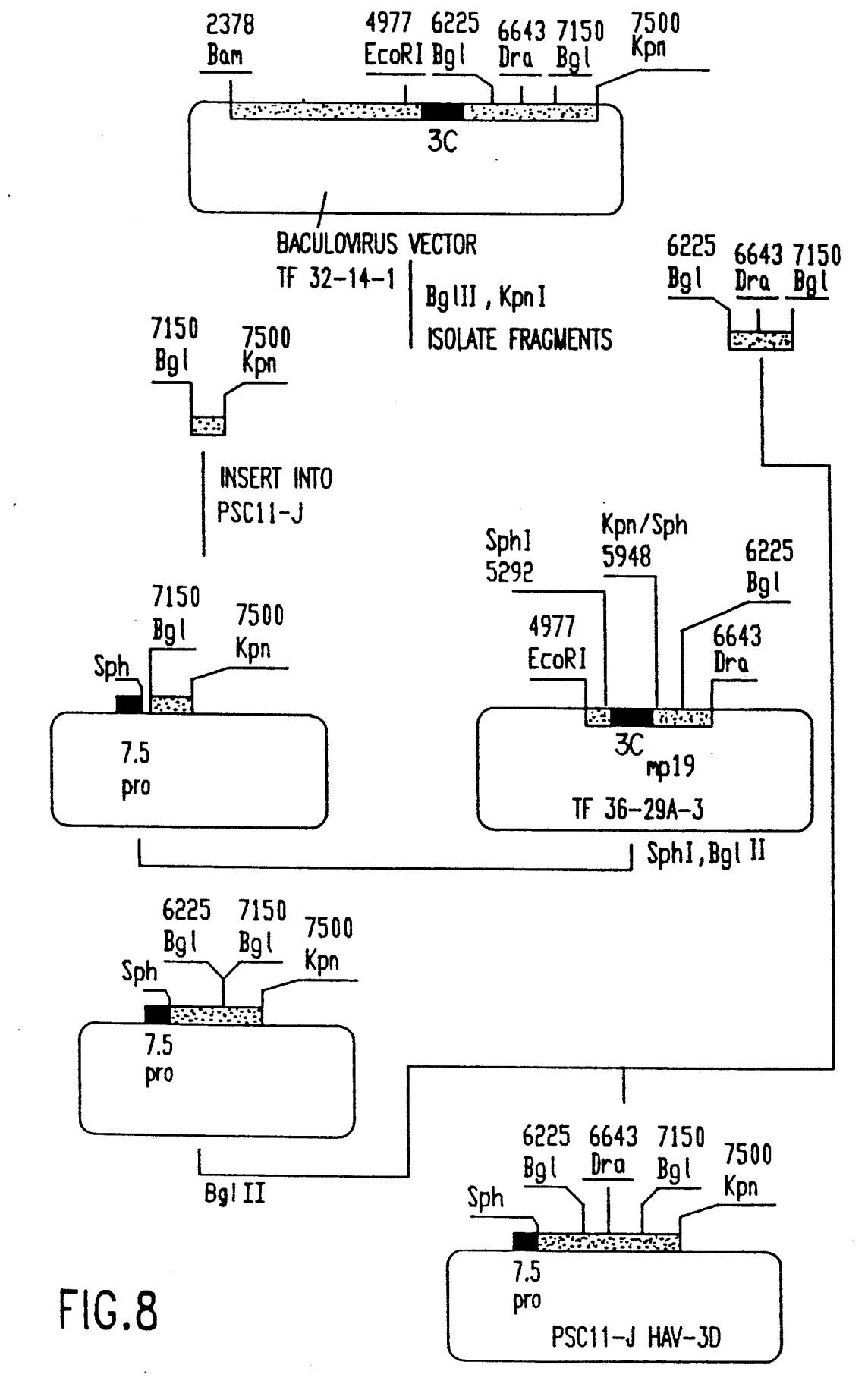

FIG. 8. Construction of vector PSC 11-J HAV-3D in which the polymerase gene of HAV consisting of nucleotide positions 6225-7500 of the HAV cDNA is cloned into a vaccinia virus vector. This construct has been provided with initiation and termination codons in order to prevent readthrough proteins from being expressed.

Figure 9:
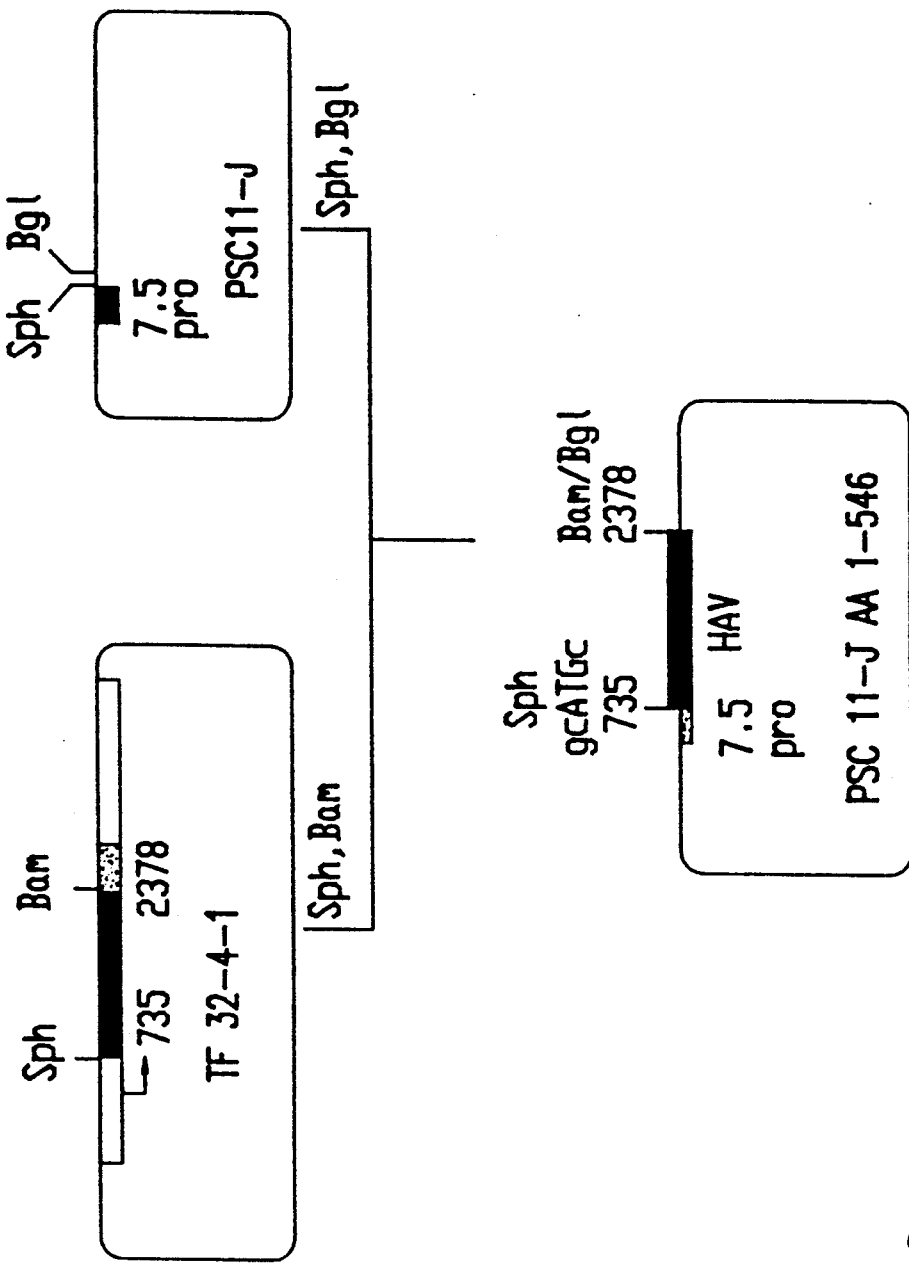

FIG. 9. Construction of vector PSC 11-J AA 1-546 in which an epitope of HAV consisting of nucleotide positions 735 to 2378 of the HAV cDNA is cloned into a vaccinia virus vector. This construct has been provided with initiation and termination codons in order to prevent readthrough proteins from being expressed.

Figure 10:
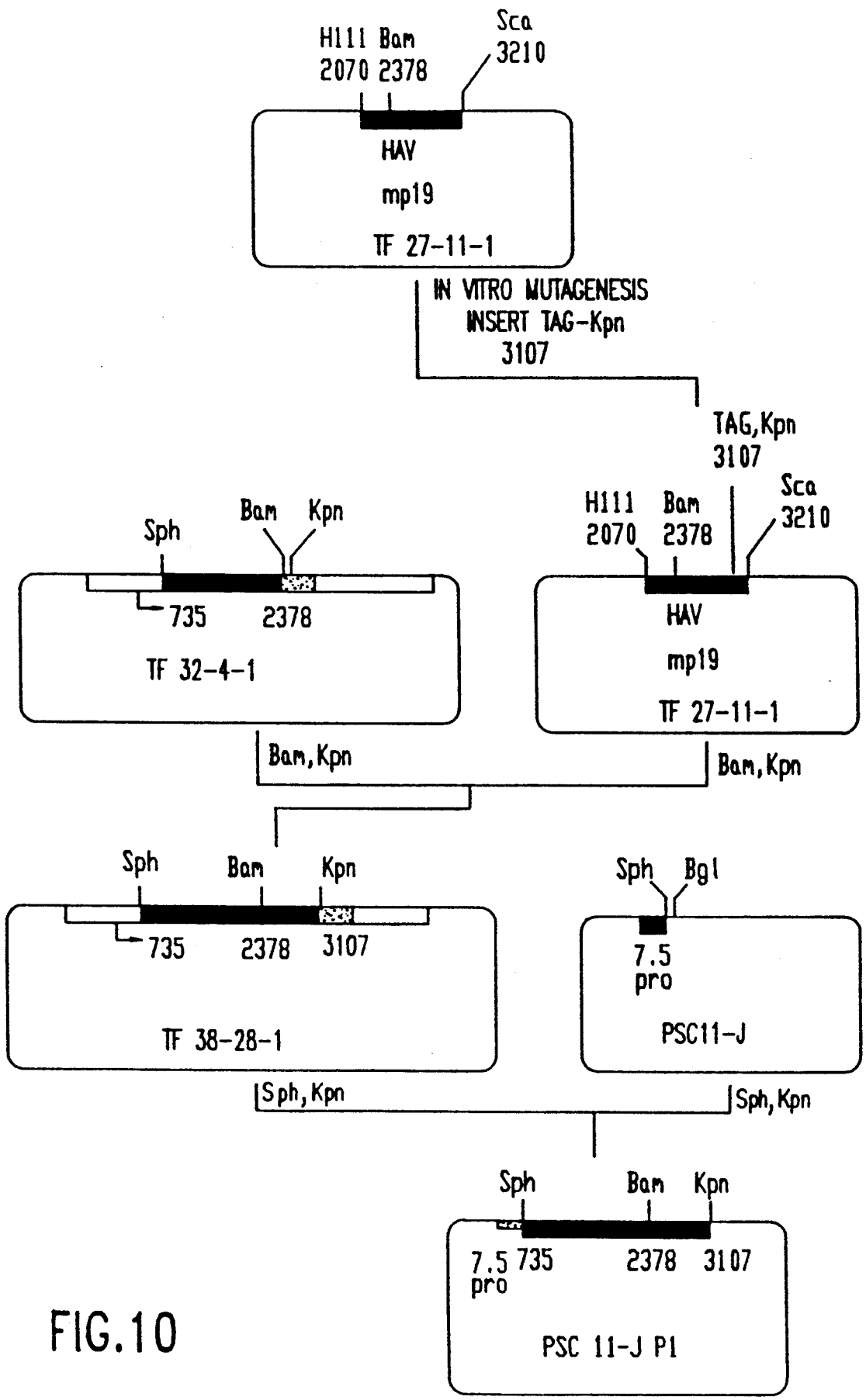

FIG. 10. Construction of vector PSC 11-J P1 in which an epitope of HAV consisting of nucleotide position 735 to 3107 of the HAV cDNA is cloned into a vaccinia virus vector.

Figure 11:
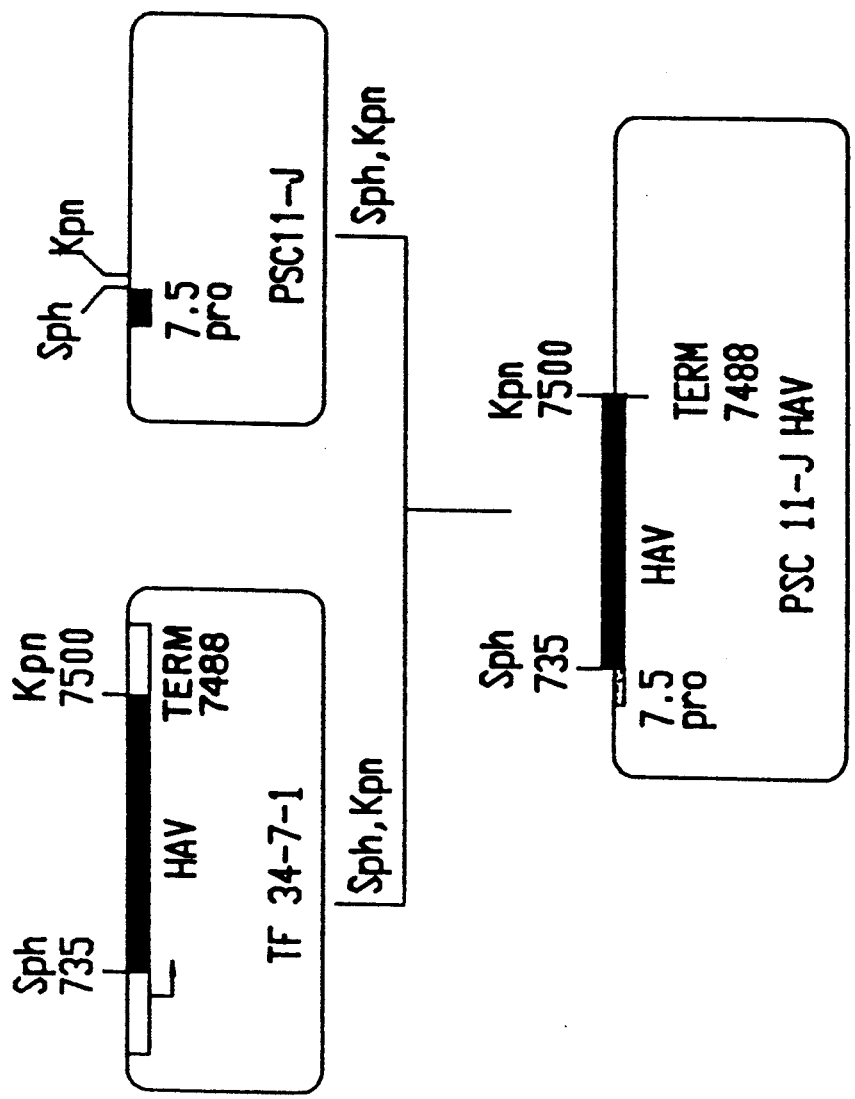

FIG. 11. Construction of vector PSC11-J HAV (pHAVTF 37-27-5) in which the epitope of HAV consisting of nucleotide positions 735 to 7488 of the HAV cDNA is cloned into a vaccinia virus vector.

Figure 12:
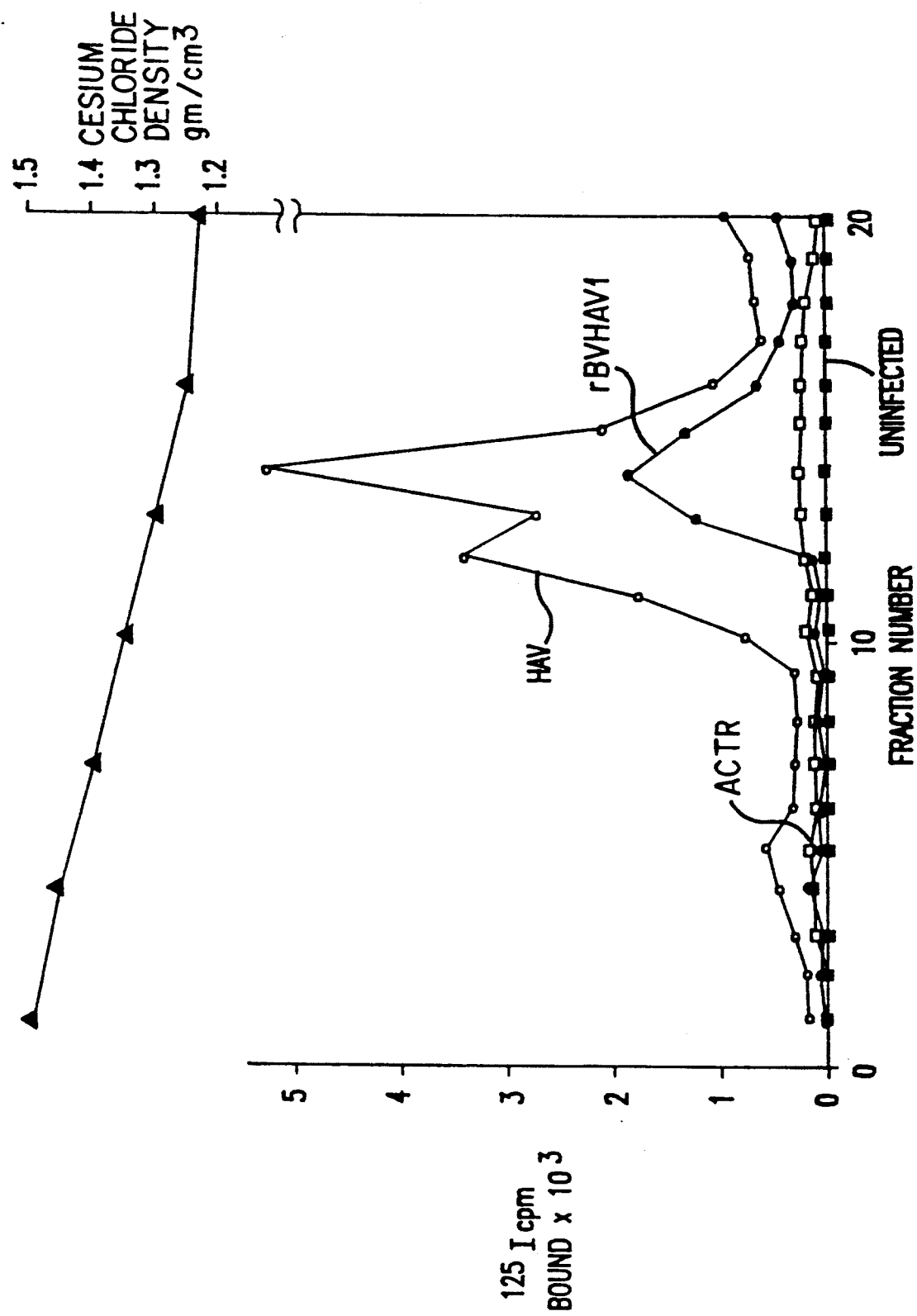

FIG. 12. 250 μl fractions were collected from self-forming cesium chloride gradients (5 ml) which contained either cell culture derived HM-175 HAV, AcTR, Uninfected Spodoptera frugiperda cells, and cells infected with the recombinant rBVHAVI (derived from pHAVTF 34-7-1). Fractions were evaluated by solid phase radioimmunoassay for HAV antigen using human convalescent sera as the capture antibody, 50 μl of cell lysate fractions or 5 μl of HAV fractions were applied, and antigen detected with $^{125}$I-labeled human convalescent IgG as previously described (Stapleton, Jansen and Lemon. Gastro 88:1427-1432, 1985). Density of gradient fractions was determined by refractive index. Symbols in FIG. 12 are as follows:

■ — Uninfected; □ — ACTR;
● — rBVHAV1; ○ — HAV.

Figure 13A:
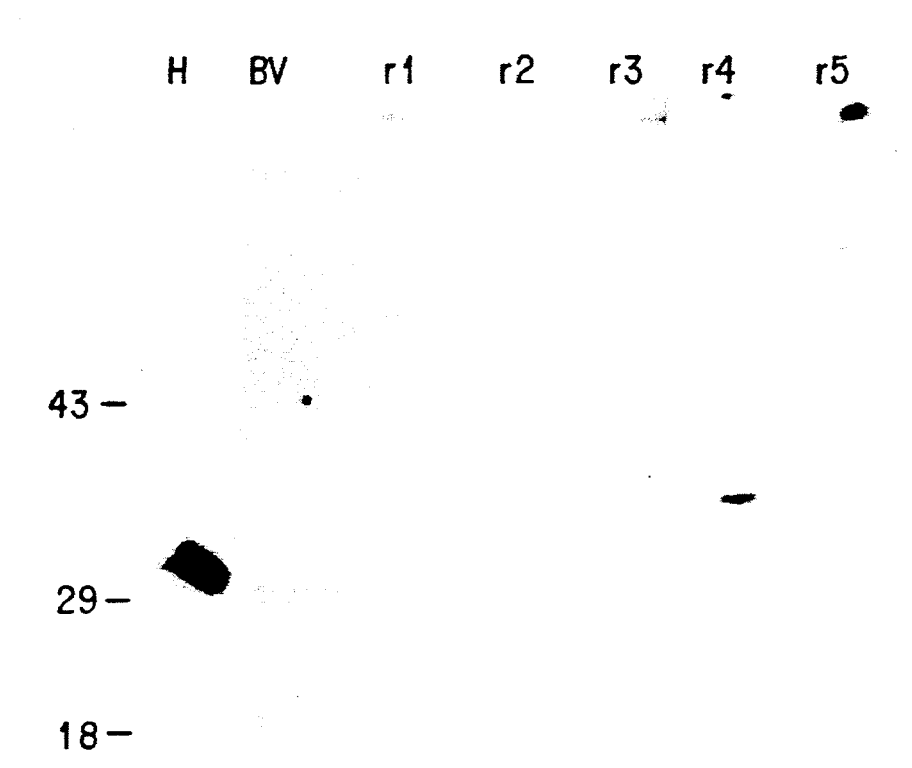

FIG. 13A. Western blot analysis of insect cell extracts infected with recombinant viruses containing the HAV polyprotein cDNA sequence that were electrophoresed on SDS polyacrylamide gels, transferred to nitrocellulose paper and probed with anti-HAV VP1 antibody. Immunoblot analysis of HAV (H), AcTR (BV), and 5 recombinant baculoviruses where the location of the translational start signal has been varied from the same location as the polyhedrin gene (r1, r2), +18 nucleotides (r3, r4), and +120 nucleotides (r5). The r3 and r4 constructs were derived from pHAVTF 34-7-1 and r5 from pHAVTF 34-7-3.

Figure 13B:
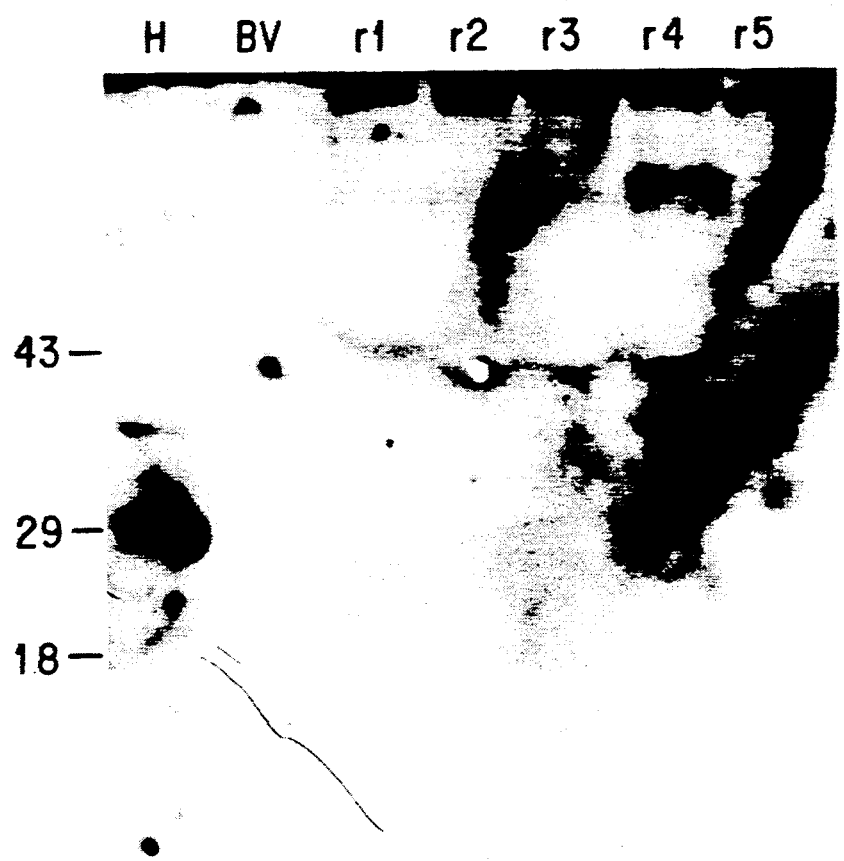

FIG. 13B. The figure in FIG. 13A was exposed for 3 days, thereby revealing that the high molecular weight bands present in the recombinants are more obvious.

Figure 14:
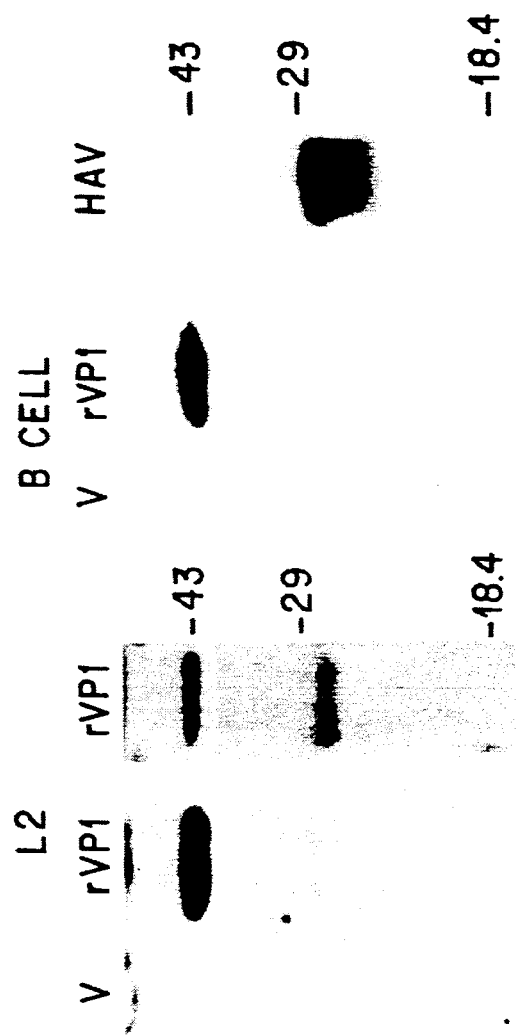

FIG. 14. Immunoblot analysis of wild type vaccinia (V) and rVP$_1$ infected mouse L-2 cells detected by rabbit anti-trpE/HAVP$_{3,1}$ serum (lanes 1 and 2), and human convalescent anti-HAV serum (lane 3). rVP1 expression in human EBV-transformed B cells is demonstrated in comparison with wild type vaccinia (V) probed with anti-trpE/HAVP$_{3,1}$ serum (lanes 4 and 5). Cell culture derived HAV probed with anti-trpE/HAVP$_{3,1}$ serum is shown in lane 6.

Figure 15:
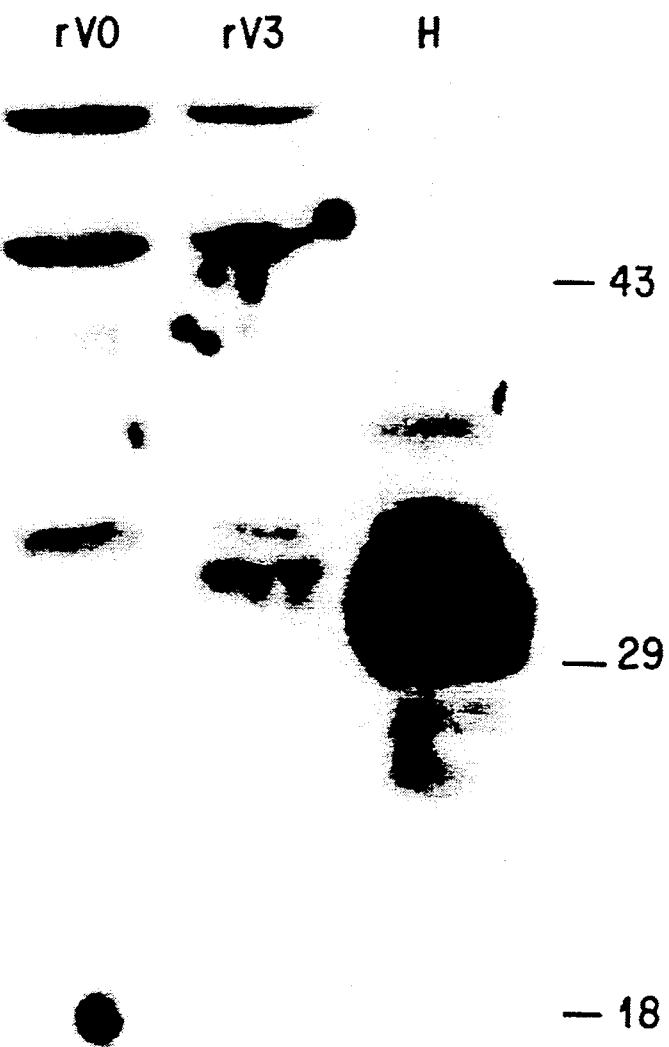

FIG. 15. Immunoblot analysis of rVP3 infected L-2 cells is shown compared with a recombinant HAV VP0 construct (rVO) which did not express VPO and cell culture derived HAV (H). Proteins were detected by anti-trpE/HAVP$_{3,1}$ serum.

Figure 16A:
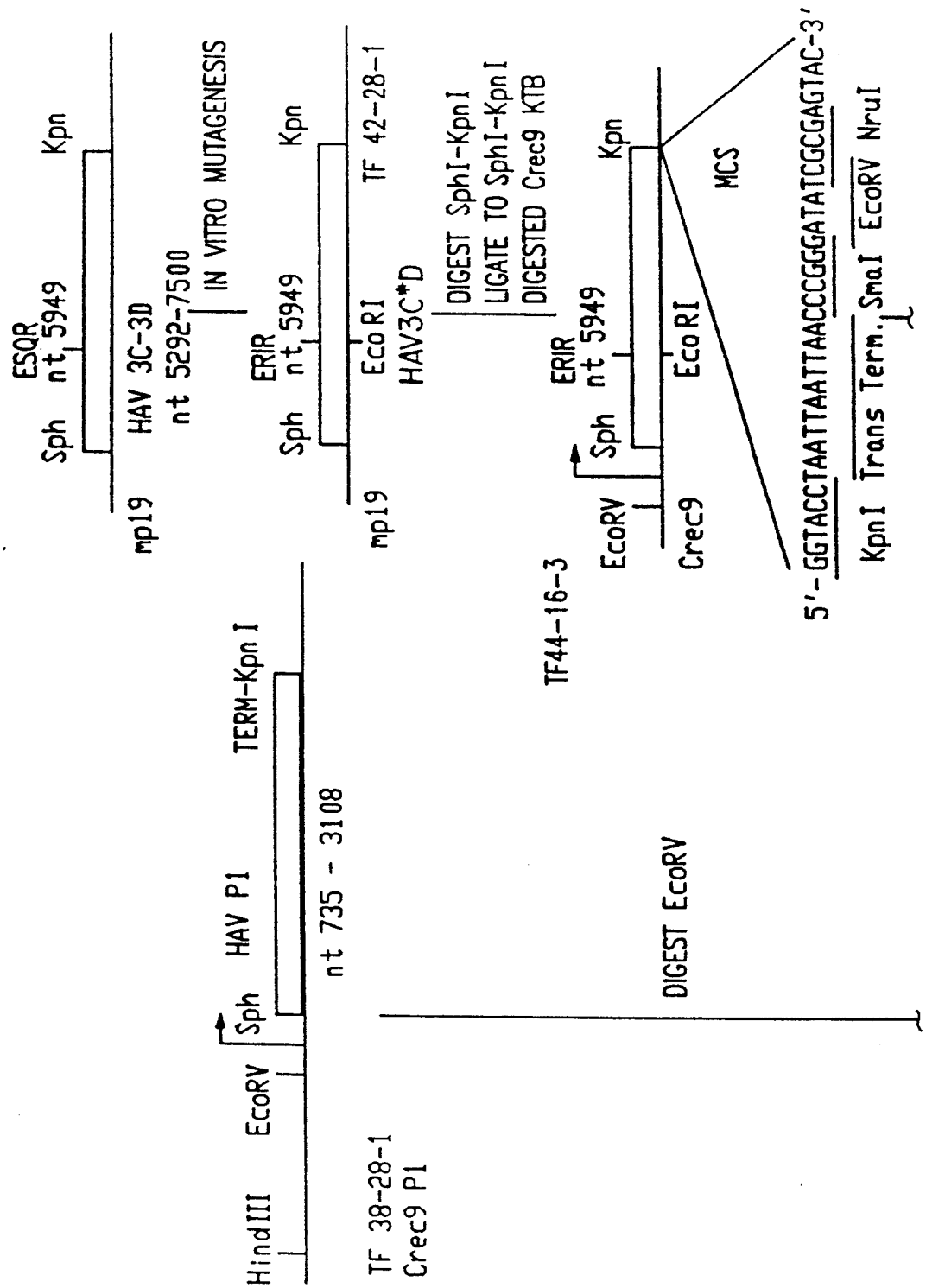
Figure 16B:
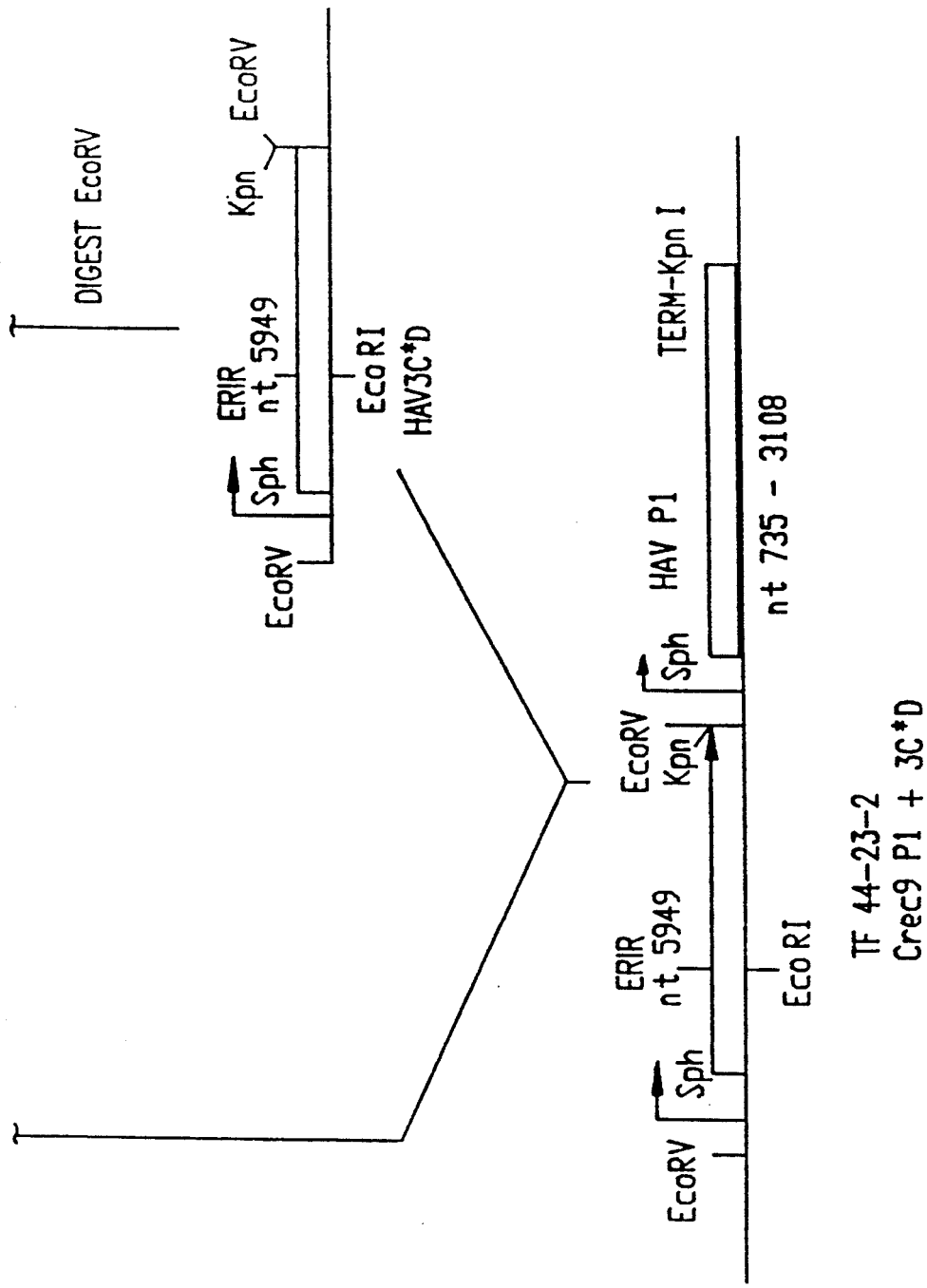

FIG. 16. Construction of vector pHAVTF 44-23-2 in which an epitope of HAV consisting of nucleotide positions 735 to 3108 and 5292 to 7500 of the HAV cDNA is cloned into a baculovirus vector. Site-directed mutagenesis was used to create an EcoRI site (GAATTC) such that the amino acids at the proposed cleavage site of the 3C+3D protease polymerase region at nucleotide positions 5945 to 5949 of the HAV genome was altered, thus rendering the 3C+3D uncleavable.

Figure 17:
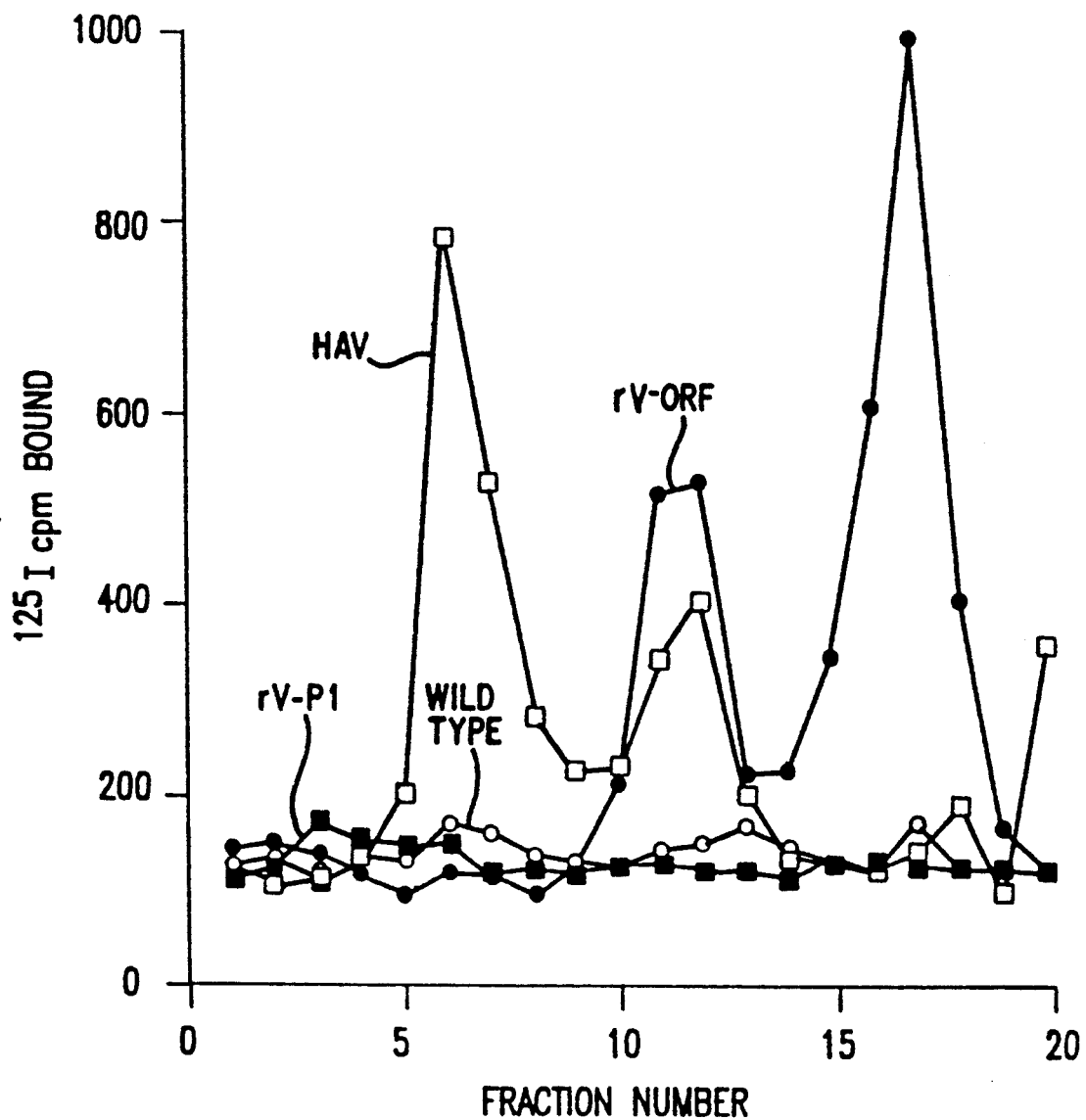

FIG. 17. 250 μl fractions were collected from sucrose gradients which contained either cell culture derived HAV, rV-ORF, wild type or rV-P1 infected cells. Fractions were evaluated by solid phase radioimmonoassay for HAV antigen using human convalescent sera as the capture antibody, HAV fractions were applied, and antigen detected with $^{125}$I-labeled human, convalescent IgG as previously described.

Figure 18A:
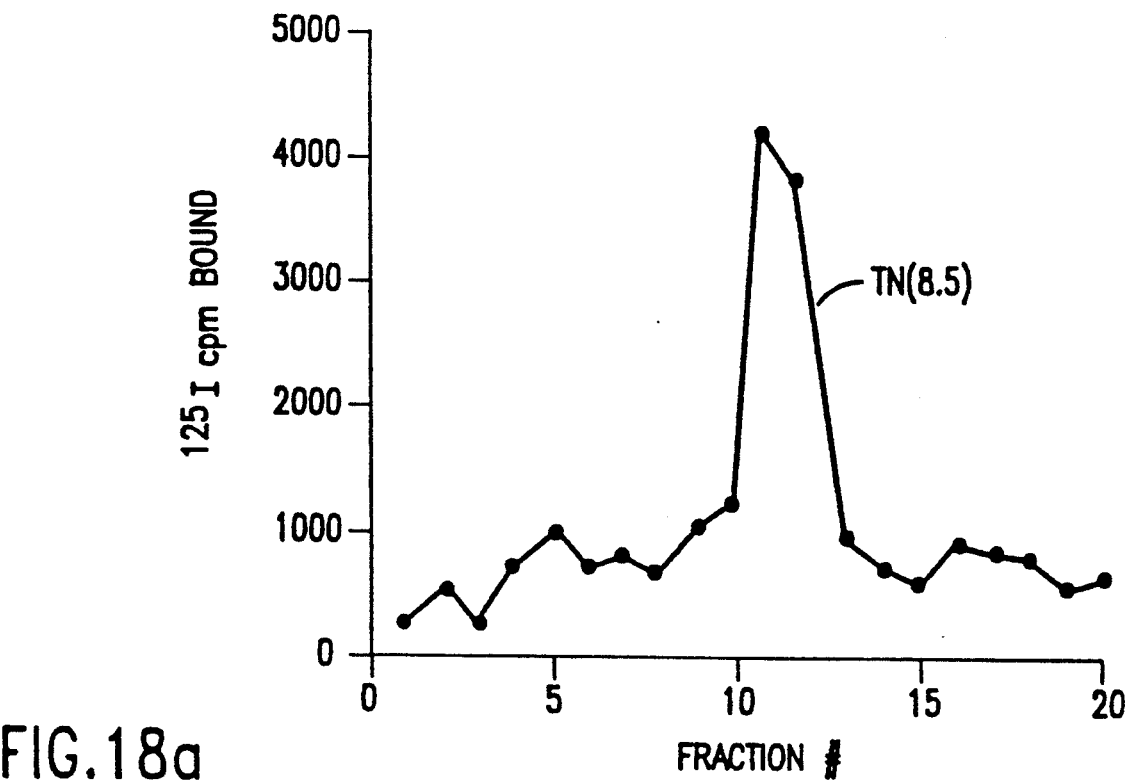

FIG. 18, PANEL A. pH 6.5 sucrose gradient analysis of HAV antigen profiles from vVAC-ORF infected cells.

FIG. 18, PANEL B. pH 7.2 sucrose gradient analysis of HAV antigen profiles from vVac-ORF infected cells.

Figure 19:
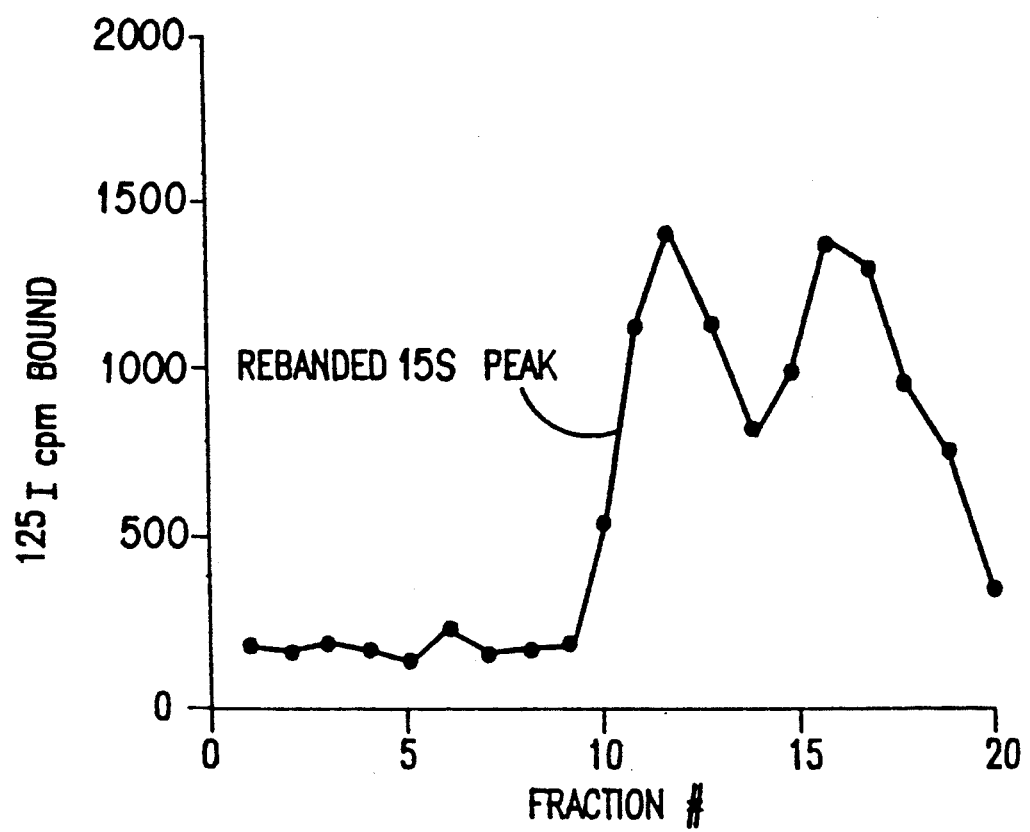

FIG. 19. Sucrose gradient analysis of 15S pentamer peaks from several gradients that were pooled and concentrated.

5. DETAILED DESCRIPTION OF THE INVENTION

The present invention relates to recombinant viruses that encode hepatitis A virus polyproteins capable of capsid formation. The recombinant HAV polyproteins of the present invention are immunogenic in immunized animals. Another embodiment of the invention relates to recombinant viruses that encode hepatitis A virus proteins. The present invention is also directed to vector/host systems that can express the recombinant HAV polyprotein gene in different hosts, including but not limited to, cultured cells or microorganisms.

The recombinant HAV of the invention which display immunogenic properties can be used in vaccine formulations. Alternatively, recombinant HAV of the invention which is antigenic can be used in diagnostic assays for detection of HAV in infected individuals. The invention is described in the subsections below in terms of (a) the ability of the recombinant HAV polypeptide to form capsid particles; (b) the ability of the recombinant HAV protease to process the recombinant VP4, 2, 3, 1 polyprotein; (c) the ability of the recombinant HAV 3C*D uncleaved protease polymerase polyprotein to process the VP4, 2, 3, 1 polyprotein, (recombinant vector HAV 3C*D contains the HAV PI precursor protein coding region and the 3C+3D protease polymerase coding region, wherein the later coding region has been mutagenized at the proposed cleavage site of the protease polymerase polyprotein); and (d) the ability of the recombinant HAV epitopes to elicit cell mediated and humoral immunity.

5.1. Cloning and Expression of Recombinant Hepatitis A Virus Polyprotein

The HAV cDNA (Cohen et al., 1987, Proc. Natl. Acad. Sci U.S.A., 84:2497-2501) may be cloned into any of a variety of cloning vectors such as the E. coli plasmid vectors pBR322 or pUC19 in order to generate copies of the gene sequence for use in the invention. Due to the degeneracy of the nucleotide coding sequences, other DNA sequences which encode substantially the same amino acid sequence as depicted in (Cohen et al., 1987, Proc. Natl. Acad. Sci. U.S.A., 84:2497-2501) can be used. These include but are not limited to nucleotide sequences depicted in (Cohen et al., 1987, Proc. Natl. Acad. Sci. U.S.A., 84:2497-2501) which are altered by the substitution of different codons that encode the same or a functionally equivalent amino acid residue within the sequence (for example, an amino acid of the same polarity), thus producing a conservative change.

Regions of the HAV polyprotein gene can be excised from the cloning vector by restriction endonuclease digestion and ligated into a compatible expression vector (see infra). In the examples described in Sections 6 and 7, infra, the baculovirus and vaccinia virus expression vectors were used. The expressed recombinant proteins are screened for reactivity with polyclonal antisera specific to native HAV, VP1 or VP3 to identify recombinant HAV polyproteins.

5.2. Construction of Expression Vectors Containing the HAV as Coding Sequence Methods which are well known to those skilled in the art can be used to construct expression vectors containing the HAV coding sequence and appropriate transcriptional/translational control signals. These methods include in vitro recombinant DNA techniques, synthetic techniques and in vivo recombination/genetic recombination. See, for example, the techniques described in Maniatis et al., 1982 Molecular Cloning A Laboratory Manual, Cold Spring Harbor Laboratory, N.Y., Chapter 12.

A variety of host-expression vector systems may be utilized to express the HAV coding sequence. These include be are not limited to microorganisms such as bacteria transformed with recombinant bacteriophage DNA, plasmid DNA or cosmid DNA expression vectors containing the HAV coding sequence; yeast transformed with recombinant yeast expression vectors containing the HAV coding sequence; insect cell systems infected with recombinant virus expression vector (e.g., baculovirus) containing the HAV coding sequence; or animal cell systems infected with recombinant virus expression vectors (e.g., adenovirus, vaccinia virus) containing the HAV coding sequence.

The expression elements of these vectors vary in their strength and specificities. Depending on the host/vector system utilized, any of a number of suitable transcription and translation elements, including constitutive and inducible promoters, may be used in the expression vector. For example, when cloning in bacterial systems, inducible promoters such as pL of bacteriophage λ, plac, ptrp, ptac (ptrp-lac hybrid promoter) and the like may be used; when cloning in insect cell systems, promoters such as the baculovirus polyhedrin promoter may be used; when cloning in mammalian cell systems, promoters derived from the genome of mammalian cells (e.g., the adenovirus late promoter; the vaccinia virus 7.5K promoter) may be used. Promoters produced by recombinant DNA or synthetic techniques may also be used to provide for transcription of the inserted HAV coding sequence.

In yeast, a number of vectors containing constitutive or inducible promoters may be used. For a review see, Current Protocols in Molecular Biology, Vol 2, 1988, Ed. Ausubel et al., Greene Publish. Assoc. & Wiley Interscience Ch. 13; Grant et al., 1987, Expression and Secretion Vectors for Yeast, in Methods in Enzymology, Eds. Wu & Grossman, 31987, Acad. Press, N.Y., Vol. 153, pp. 516–544; Glover, 1986, DNA Cloning, Vol. II, IRL Press, Wash., D.C. Ch.3; and Bitter, 1987, Heterologous Gene Expression in Yeast, Methods in Enzymology, Eds. Berger & Kimmel, Acad. Press, N.Y., Vol. 152, pp. 673–684; and The Molecular Biology of the Yeast Saccharomyces, 1982, Eds. Strathern et al., Cold Spring Harbor Press, Vols. I and II. For complementation assays in yeast, pea cDNAs for HAV may be cloned into yeast episomal plasmids (YEp) which replicate autonomously in yeast due to the presence of the yeast 2 μ circle. The HAV sequence may be cloned behind either a constitutive yeast promoter such as ADH or LEU2 or an inducible promoter such as GAL (Cloning in Yeast, Chpt. 3, R. Rothstein In; DNA Cloning Vol. 11, A Practical Approach, Ed. DM Glover, 1986, IRL Press, Wash., D.C.). Constructs may contain the 5' and 3' non-translated regions of the cognate HAV mRNA or those corresponding to a yeast gene. YEp plasmids transform at high efficiency and the plasmids are extremely stable. Alternatively vectors may be used which promote integration of foreign DNA sequences into the yeast chromosome.

A particularly good expression system which could be used to express HAV is an insect system. In one such system, *Autographa californica* nuclear polyhedrosis virus (AcNPV) is used as a vector to express foreign genes. The virus grows in *Spodoptera frugiperda* cells. The HAV coding sequence may be cloned into non-essential regions (for example the polyhedrin gene) of the virus and placed under control of an AcNPV promoter (for example the polyhedrin promoter). Successful insertion of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed. (E.g., see Smith et al., 1983, J. Viol. 46:586; Smith, U.S. Pat. No. 4,215,051).

In cases where an adenovirus is used as an expression vector, the HAV coding sequence may be ligated to an adenovirus transcription/translation control complex, e.g., the late promoter and tripartite leader sequence. This chimeric gene may then be inserted in the adenovirus genome by in vitro or in vitro recombination. Insertion in a non-essential region of the viral genome (e.g., region E1 or E3) will result in a recombinant virus that is viable and capable of expressing HAV in infected hosts. (E.g., See Logan & Shenk, 1984, Proc. Natl. Acad. Sci. (U.S.A.) 81:3655-3659). Alternatively, the vaccinia 7.5K promoter may be used. (E.g., see Mackett et al., 1982, Proc. Natl. Acad. Sci. (U.S.A.) 79:7415-7419; Mackett et al., 1984, J. Virol. 49:857-864; Panicali et al., 1982, Proc. Natl. Acad. Sci. 79:4927-4931).

Specific initiation signals may also be required for efficient translation of inserted HAV coding sequences. These signals include the ATG initiation codon and adjacent sequences. In cases where the entire HAV genome, including its own initiation codon and adjacent sequences, are inserted into the appropriate expression vectors, no additional translational control signals may be needed. However, in cases where only a portion of the HAV coding sequence is inserted, exogenous translational control signals, including the ATG initiation codon, must be provided. Furthermore, the initiation codon must be in phase with the reading frame of the HAV coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bitter et al., 1987, Methods in Enzymol. 153:516-544).

In addition, a host cell strain my be chosen which modulates the expression of the inserted sequences, or modifies and processes the gene product in the specific fashion desired. Expression driven by certain promoters can be elevated in the presence of certain inducers, (e.g., zinc and cadmium ions for metallothionein promoters). Therefore, expression of the genetically engineered HAV may be controlled. This is important if the protein product of the cloned foreign gene is lethal to host cells. Furthermore, modifications (e.g., glycosylation) and processing (e.g., cleavage) of protein products may be important for the function of the protein. Different host cells have characteristic and specific mechanisms for the post-translational processing and modification of proteins. Appropriate cells lines or host systems can be chosen to ensure the correct modification and processing of the foreign protein expressed.

5.3 Identification of Transfectants or Transformants Expressing the HAV Gene Product and Isolation of HAV The host cells which contain the HAV coding sequence and which express the biologically active HAV gene products may be identified by at least four general approaches: (a) DNA-DNA hybridization; (b) the presence or absence of "marker" gene functions; (c) assessing the level of transcription as measured by the expression of HAV mRNA transcripts in the host cell; and (d) detection of the HAV gene products as measured by immunoassay or by its biological activity.

In the first approach, the presence of the HAV coding sequence inserted in the expression vector can be detected by DNA-DNA hybridization using probes comprising nucleotide sequences that are homologous to the HAV coding sequence substantially as described (Cohen et al., 1987, J. Viral 61:50-59), portions or derivatives thereof.

In the second approach, the recombinant expression vector/host system can be identified and selected based upon the presence or absence of certain "marker" gene functions (e.g., thymidine kinase activity, resistance to antibiotics, resistance to methotrexate, transformation phenotype, occlusion body formation in baculovirus, etc.). For example, if the HAV coding sequence is inserted within a marker gene sequence of the vector, recombinants containing the HAV coding sequence can be identified by the absence of the marker gene function. Alternatively, a marker gene can be placed in tandem with the HAV coding sequence under the control of the same or different promoter used to control the expression of the HAV coding sequence. Expression of the market in response to induction or selection indicates expression of the HAV coding sequence.

In the third approach, transcriptional activity for the HAV coding region can be assessed by hybridization assays. For example, RNA can be isolated and analyzed by Northern blot using a probe homologous to the HAV coding sequence or particular portions thereof substantially as described (Cohen et al., 1987, J. Vivol 61:50-59). Alternatively, total nucleic acids of the host cell may be extracted and assayed for hybridization to such probes.

In the fourth approach, the expression of the HAV protein product can be assessed immunologically, for example by Western blots, immunoassays such as radioimmunoprecipitation, enzyme-linked immunoassays and the like. The ultimate test of the success of the expression system, however, involves the detection of the biologically active HAV gene product. Where the host cell secretes the gene product, the cell free media obtained from the cultured transfectant host cell may be assayed for HAV activity. Where the gene product is not secreted, cell lysates may be assayed for such activity.

5.4. Identification and Purification of the Expressed Gene Product

Once a recombinant that expresses the HAV protein or fragment thereof is identified, the gene product should be analyzed. This can be achieved by assays based on the physical, immunological or functional properties of the product. Immunological analysis is especially important where the ultimate goal is to use the gene products or recombinant viruses that express such products in vaccine formulations and/or as antigens in diagnostic immunoassays.

Antisera specific to native HAV, VP1, and VP3 are available for analyzing the immunoreactivity of the recombinant HAV product. In addition, antiserum specific to HAV should be neutralizing.

The protein should be immunoreactive whether it results from the expression of the entire gene sequence, a portion of the gene sequence or from two or more gene sequences which are ligated to direct the production of chimeric proteins. This reactivity may be demonstrated by standard immunological techniques, such as radioimmunoprecipitation, radioimmune competition, or immunoblots.

Once the recombinant HAV polyprotein is identified, capsids can be isolated and purified by a single CsCl gradient centrifugation (see Section 6.1.3. infra).

5.5. Determination of the Immunopotency of the Recombinant Product

Immunopotency of the HAV related product can be determined by monitoring the immune response of test animals following immunization with the purified protein, synthetic peptide or protein. In cases where the HAV related protein is expressed by an infectious recombinant virus, the recombinant virus itself can be used to immunize test animals. Test animals can include but are not limited to mice, rats, rabbits, primates, and eventually human subjects. Methods of introduction of the immunogen can include oral, intradermal, intramuscular, intraperitoneal, intravenous, subcutaneous, intranasal or any other standard routes of immunizations. The immune response of the test subjects can be analyzed by four approaches: (a) the reactivity of the resultant immune serum to authentic viral antigens, as assayed by known techniques, e.g., enzyme linked immunosorbant assay (ELISA), immunoblots, radioimmunoprecipitations, etc., (b) the ability of the immune serum to neutralize HAV infectivity in vitro (see Section 7.2.3, infra), (c) stimulation of cell mediated immune response, (Section 7.2.4, infra) and (d) protection from Hepatitis A virus infection.

5.6. Formulation of Vaccine

Many methods can be used to administer the vaccine formulations described herein to an animal or a human. These include, but are not limited to: oral, intradermal, intramuscular, intraperitoneal, intravenous, subcutaneous and intranasal routes. The secretory IgA antibodies produced by the mucosal associated lymphoid tissue can play a major role in protection against Hepatitis A virus infection by preventing the initial interaction of the pathogens with the mucosal surface, or by neutralizing the important epitopes of the pathogens that are involved in infection/or spreading of the disease. Stimulation of mucosal immune responses, including production of secretory IgA antibodies can be of major importance in conferring protection against lower and upper respiratory tract infection. When a live recombinant virus vaccine formulation is used, it may be administered via the natural route of infection of the parent wild-type virus which was used to make the recombinant virus in the vaccine formulation.

5.6.1 Capsid or Pentamer Vaccine Formulation

One purpose of the present invention is to provide empty capsid or pentamer vaccines which are used to protect against disease symptoms of hepatitis A virus. The empty capsid or pentamer vaccines are prepared from recombinant vaccinia HAV or baculovirus HAV infected cells. Recombinant viruses encoding the entire coding region of HAV or the P1 precurser plus the protease polymerase or mutants of the protease polymerase polyproteins will direct the expression of HAV polypeptides which are properly processed and formed pentamers or empty capsids. For example, recombinant vectors encoding nucleotides 735 to 7488 (pHAVTF 34-7-1, pHAVTF 34-7-3 and pHAVTF 37-27-5) or encoding nucleotides 735 to 3107 and 5292 to 7500 (pHAVTF 44-23-2) of HAV are all capable of producing empty capsid particles, or pentamers in the appropriate expression system, described supra, section 5.2 and 5.3. Vaccines prepared from recombinant capsids or pentamers, which are capable of eliciting a protective immune response, are advantageous because there is no risk of infection to the recipients.

The HAV empty capsid particles or pentamers can be purified from recombinants that express the HAV coding region. Such recombinants include but are not limited to any of the previously described bacteria for yeast transformants, cultured insect cells infected with recombinant HAV baculoviruse or cultured mammalian cells that express HAV capside particles.

The HAV empty capsid particles or pentamers are adjusted to an approriate concentration and can be formulated with any suitable vaccine adjuvant. The polypeptides and proteins may generally be formulated at concentrations in the range of 0.1 mg to 100 mg per kg/host. Physiologically acceptable media may be used as carriers. These include, but are not limited to: sterile water, saline, phosphate buffered saline and the like. Suitable adjuvants include, but re not limited to: surface active substances, e.g., hexadecylamine, octadecylamine, actadecyl amino acid esters, lysolecithin, dimethyl-dioctadecylammonium bromide, N,N-dioctadecyl-N'-N'bis(2-hydroxyethylpropane diamine), methoxyhexadecyglycerol, and pluronic polyols; polyamines, e.g., pyran, dextransulfate, poly IC, polyacrylic acid, carbopol; peptides, e.g., muramyl dipeptide, dimethylglycine, tuftsin; oil emulsions; and Thus, the subject invention provides compositions comprising pentamers or empty capsid, i.e., capsid particles devoid of full length HAV RNA, wherein such compositions are free of capids have full length HAV RNA. Also, the subject invention provides such compositions as a component in an HAV vaccine formulation. mineral gels, e.g., aluminum hydroxide, aluminum phosphate, etc.

5.6.2. Subunit Vaccine Formulations

The proteins and polypeptides of the present invention that are related to neutralizing epitope(s) of the HAV are useful immunogens in a subunit vaccine to protect against disease symptoms of HAV infection. Subunit vaccines comprise solely the relevant immunogenic material necessary to immunize a host. Vaccines prepared from genetically engineered immunogens of HAV proteins or fragments thereof, which are capable of eliciting a protective immune response, are particularly advantageous because there is no risk of infection to the recipients.

Thus, the HAV related proteins and polypeptides can be purified from recombinants that express the neutralizing epitopes. Such recombinants include but are not limited to any of the previously described bacteria or yeast transformants, cultured insect cells infected with recombinant HAV baculoviruses or cultured mammalian cells that express HAV protein epitopes.

The HAV related proteins or polypeptides are adjusted to an appropriate concentration and can be formulated with any suitable vaccine adjuvant. The polypeptides and proteins may generally be formulated at concentrations in the range of 0.1 mg to 100 mg per kg/host. Physiologically acceptable media may be used as carriers. These include, but are not limited to: sterile water, saline, phosphate buffered saline and the like. Suitable adjuvants include, but re not limited to: surface active substances, e.g., hexadecylamine, octadecylamine, actadecyl amino acid esters, lysolecithin, dimethyl-dioctadecylammonium bromide, N,N-dioctadecyl-N'-N'bis(2-hydroxyethylpropane diamine), methoxyhexadecyglycerol, and pluronic polyols; polyamines, e.g., pyran, dextransulfate, poly IC, polyacrylic acid, carbopol; peptides, e.g., muramyl dipeptide, dimethylglycine, tuftsin; oil emulsions; and mineral gels, e.g., aluminum hydroxide, aluminum phosphate, etc. The immunogen may also be incorporated into liposomes or conjugated to polysaccharides and/or other polymers for use in a vaccine formulation.

In yet another embodiment of this mode of the invention, the related protein, or polypeptide is a hapten, i.e., a molecule which is antigenic in that it reacts specifically or selectively with cognate antibodies, but is not immunogenic in that it cannot elicit an immune response. In such case, the hapten may be covalently bound to a carrier or immunogenic molecule; for example, a large protein such as protein serum albumin will confer immunogenicity to the hapten coupled to it. The hapten-carrier may be formulated for use as a subunit vaccine.

The polypeptides and proteins of the present invention may be used when linked to a soluble macromolecular carrier. Preferably, the carrier and the polypeptides and proteins of the present invention are in excess of five thousand daltons after linking. More preferably, the carrier is in excess of five kilodaltons. Preferably, the carrier is a polyamino acid, either natural or synthetic, which is immunogenic in animals, including humans. The manner of linking is conventional. Many linking techniques are disclosed in U.S. Pat. No. 4,629,783 which is incorporated herein by reference. Many cross-linking agents are disclosed in 1986-87 Handbook And General Catalog, Pierce Chemical Company, (Rockford, Ill.) pages 311 to 340, which pages are incorporated herein by reference.

5.6.3. Viral Vaccine Formulations

Another purpose of the present invention is to provide either a live recombinant viral vaccine or an inactivated recombinant viral vaccine, which is used to protect against disease symptoms of hepatitis A virus. To this end, recombinant viruses are prepared that express HAV protein related epitopes (see Section 4, supra). Where the recombinant virus is infectious to the host to be immunized but does not cause disease, a live vaccine is preferred because multiplication in the host leads to a prolonged stimulus, therefore, conferring substantially long-lasting immunity. The infectious recombinant virus when introduced into a host can express the HAV related protein or polypeptide fragments from its chimeric genes and, thereby, elicit an immune response against HAV antigens. In cases where such an immune response is protective against subsequent HAV infection, the live recombinant virus, itself, can be used in a preventative vaccine against HAV infection. Production of such recombinant virus may involve both in vitro (e.g., tissue culture cells) and in vivo (e.g., natural host animal) systems. For instance, conventional methods for preparation and formulation of smallpox vaccine may be adapted for the formulation of live recombinant virus vaccine expressing HAV related proteins or polypeptides. Multivalent live virus vaccines can be prepared from a single or a few infectious recombinant viruses that express epitopes of organisms that cause disease in addition to the epitopes of HAV. For example, a vaccinia virus can be engineered to contain coding sequences for other epitopes in addition to those of HAV. Such a recombinant virus itself can be used as the immunogen in a multivalent vaccine. Alternatively, a mixture of vaccinia or other viruses, each expressing a different gene encoding for an epitope of HAV and an epitope of another disease causing organism can be formulated in a multivalent vaccine.

The following Examples are offered for the purpose of illustrating the present invention and are not to be construed to limit the scope of the present invention.

6. EXAMPLE: EXPRESSION OF RECOMBINANT HAV IN A BACULOVIRUS SYSTEM

6.1 Materials and Methods 6.1.1. Construction of Recombinant Plasmids

The sequence encoding the HAV polyprotein begins at nucleotide 735 of the HAV genome. An SphI site (GCATGC) was engineered into the site such that the ATG of the restriction site correspond to the initiation methionine of the HAV polyprotein. This new SphI site was then used to insert the HAV polyprotein gene into an SphI site downstream of the polyhedrin promoter that is present in different baculovirus transfer vectors. The detailed description of the construction of these vectors are described in FIGS 2 to 4.

6.1.2. Preparation of Recombinant Baculoviruses

Recombinant viruses containing the HAV polyhedrin under the control of the polyhedrin promoter were constructed using what are now standard protocols. $3 \times 10^6$ insect cells were plated in 60 mm tissue culture plates. Approximately 0.1 ug of wild type viral DNA and 1-5 ug of transfer plasmid DNA were used to co-transfect insect cell using the Lipofectin Reagent (Bethesda Research Laboratory, Gathersburg, Md.) using the manufacturers protocols. The reagent and DNA were added to the cells overnight. The reagent, DNA and media were removed and the cells incubated in fresh media for three to four days. Progeny virus were then examined in agarose overlays. Putative recombinants that expressed an occlusion body negative phenotype (dull, non-refractile plaques) were picked, resuspended in fresh media and replated. After three rounds of plaque purification, the recombinant viruses were used to infect insect cell cultures to produce viral stock supernatants. Radiolabeled HAV cDNA was used in Southern blot analysis for screening to determine that recombinants contained the HAV polyprotein coding region.

6.1.3. Isolation of Recombinant Hepatitis A Virus Capsids

S. frugiperda cells were infected with the recombinant baculovirus A virus at a multiplicity of 5 to 10 plaque forming units (p.f.u.)/cell and harvested at either 4 or 5 days post-infection. The cells were washed twice with PBS, resuspended in 10 mM-Tris-HCl buffer pH 7.4 and sonicated until lysis occurred. After low speed centrifugation to remove cellular debris, the lysis was extracted (twice with fluorocarbon (1.1.2-trisloroti-fluorothane. Aldrich), the aqueous layer recovered and centrifuged at 40000 r.p.m. for 1 h. The pelleted material was resuspended in PBS and layered on a preformed, discontinuous CsCl gradient (made up in PBS (using layers of 3 ml. 4 ml and 4 ml of densities, 1.4, 1.4 and 1.2 g/ml respectively). The gradient was centrifuged at 40000 r.p.m. for 17 h in a Type 70.1 Beckman rotor. The visible fractions containing virus particles were identified by RIA, diluted and either repurified by gradient centrifugation or pelleted and resuspended in 10 mm-Tris-HCl buffer pH 7.4. Protein estimates were made using bovine serum albumin as a standard.

6.1.4. Protein Immunoblot (Western Blot) Analysis

S. frugiperda cells were infected with recombinant baculoviruses at multiplicities of 5 to 10 p.f.u./cell and incubated for 48 h at 28° C. Mock-infected or virus-infected cells were washed twice with PBS and extracted for protein. Recombinant protein samples of cell extracts or recombinant HAV particles were resolved by SDS-PAGE, after which each gel was treated for 30 min with buffer (25 mm-Tris-HCl, 192 mm glycine in 20% methanol, pH 8.3). For Western blot analyses the proteins were transferred by electroblotting for 3 h at 0.8 mA/cm$^2$ using a Sartoblot II (Sartorius) and the semi-dry transfer procedure described by Kyhse-Andersen (1984) using an Immunobilon transfer membrane (millipore), pretreated for 15 s with 100% methanol and then treated for 10 min with the electroblotting buffer. The membrane was placed in a blocking solution consisting of 5% skimmed milk and 0.05% Tween-20 made up in PBS and left overnight at 4° C. Individual or mixed rabbit polyclonal anti-VP3 VP1 antibody diluted in blocking solution was added for 1 h. Membranes were washed with 0.05% Tween 20 in PBS before reaction with goat anti-rabbit or anti-mouse immunoglobulins conjugated with alkaline phosphatase. After 1 h and multiple washings, the bound enzyme was assayed using $\beta$-naphthyl phosphate (Sigma) according to the manufacturer's instructions.

The sections below describe the construction of the HAV capsid in a recombinant system allowing discontinuous epitopes to be positioned correctly in their native configuration, thereby providing potential as a vaccine.

HAV contains a plus stranded RNA genome of approximately 7500 nucleotides packaged in a nonenveloped icosahedral capsid. Translation of the RNA yields a polyprotein which is processed to produce a variety of viral structural proteins and enzymes. The structural proteins include, VP1, VP2, VP3 and possibly VP4 which compose the capsid. In addition, the polyprotein includes proteases which are presumably involved in the processing of the polyprotein into constituent proteins. The entire HAV polyprotein was expressed in a baculovirus expression system.

6.2. Results

Putative recombinants were characterized by Southern blot analysis. DNA from infected cells was purified and digested with Eco RV and Kpn I. If the entire HAV sequence was inserted into the baculovirus genome, then the insert would be flanked by an Eco RV site in the polyhedrin promoter and a Kpn I site just 3' of the HAV polyprotein sequence (see FIGS. 2 & 3). Thus an Eco RV-RpnI digest of a HAV recombinant would produce a new restriction fragment approximately the size of the HAV insert. Southern blot analysis screening for this new restriction fragment was used to identify several recombinants containing the entire polyprotein sequence including V414.4A1 derived from TF 34-7-1 vector and V419.1A1 derived from TF 34-7-3 vector.

Recombinant viruses containing the HAV polyprotein insert were used to infect Spodoptera frugiperda cells in cell culture. Four days after infection cells were harvested and lysates analyzed for HAV proteins. The results in FIGS. 3A and 3B represent a Western blot probed with an anti-HAV VP1 antibody. The antibody reacts with recombinant strains V414.4A1 and V419.1A1 which test positive for HAV sequences by Southern analysis. In contrast, lysates of V418 which test negative in Southern analysis do not interact with the anti-HAV antibody.

The results of the Western blot indicate that the antibody interacts with a series of HAV bands. There is a band that does not enter the gel, a band at approximately 90 kd, a band at 55 kd and another at 30 kd. These bands correspond to the presence of VP1 (30 kd) and a series of processing intermediates involved in the generation of the polyprotein of 200 kd. The polyprotein is processed into segments P1, P2 and P3 in which ($-90$ kd) contains the capsid proteins VP1, VP2, VP3 and VP4. P1 is then cleaved between VP2 and VP3 to generate a VP3−VP1 intermediate (55 kd). Proteolytic cleavage of this fragment generates VP3 (25 kd) and VP1 (30 kd). Thus, antibodies generated to VP1 would be expected to react with mature VP1, the VP3−VP1 intermediate, the P1 fragment and the entire polyprotein.

7. EXAMPLE: EXPRESSION OF RECOMBINANT HAV IN A VACCINIA VIRUS SYSTEM 7.1. Materials & Methods 7.1.1. Viruses Wild type vaccinia was purchased from the ATCC and passaged in HeLa cells. HM-175 strain HAV was grown in FRhK/4 cells (passage #91-129).

7.1.2. Cells

HeLa cells were grown in Eagles MEM with 10% fetal calf serum, penicillin and streptomycin. Human TK-143 cells were used for selection of recombinant vaccinia viruses and were grown in Eagles MEM supplemented with 8% fetal calf serum and 100 micrograms/ml of 5 bromodeoxyuridine (Sigma Chemicals, St. Louis). Mouse L-2 cells were used for recombinant vaccinia virus propagation and were grown in Dulbeccos MEM-high glucose media containing 12.5% fetal calf serum supplemented with penicillin and streptomycin. Human Epstein-Barr Virus transformed B cell lines were also used for recombinant vaccinia virus propagation and were grown in RPMI 1640 supplemented with glutamine, 20% fetal calf serum, penicillin and streptomycin. BS-C-1 cells (passage #31-53) were used for HAV neutralization studies as described below. FRhk/4 cells (passage #91-129) were grown in RPMI 1640, 5% fetal calf serum, penicillin, streptomycin and glutamine.

7.1.3. Transformation of Human B Cells

Human peripheral blood mononuclear cells were isolated from a patient recently infected with HAV by ficoll-hypaque gradient centrifugation. Cells were suspended in a cell supernatant fluid containing Epstein- Barr virus (ATCC). After a 4 hour incubation cyclosporin A was added for a final concentration of 1 microgram/microliter. Cells were grown at 37 degrees C with 5% CO2. (Bird et al., 1981, *Nature*, 289:300-301).

7.1.4. Plasmid DNA

Double stranded M13mp18 and M13mp19 were obtained from New England Biolabs. Vaccinia plasmid pSC11 was generously provided by B. Moss. NIAID, NIH, HAV plasmid pHAV1307 was a gift from J. Ticehurst (1983, *Proc. Natl. Acad. Sci. U.S.A.*, 80: 5885-5889). Plasmid pHAV7 was provided by J. Cohen (1987, *J. Virol.*, 61: 3035-3039). Plasmid recombinants were constructed as described in the results and were used to transform competent DH5 alpha Escherichia coli by standard methods (Maniatis, T., Fritsch, E. F., Sambrook, J., 1982, Molecular Cloning A Laboratory Manual Cold Spring Harbor Laboratory, Cold Spring Harbor, N.Y.). Recombinant plasmids were isolated using the alkaline method and plasmid DNA was purified by cesium chloride-ethidium bromide equilibrium density gradient centrifugation. (Maniatis et al., 1982).

7.1.5. Oligonucleotide Directed Mutagenesis

Mutagenesis was performed as described by Kunkel, T. A. (1985, *Proc. Natl. Acad. Sci. U.S.A.*, 82: 488-492). Synthetic oligonucleotides containing new restriction sties and translation initiation codons were synthesized and purified by polyacrylamide gel electrophoresis. Oligonucleotides were electroeluted and kinased prior to use (Maniatis et al., 1982). Uracil containing M13mp18 or M13mp19 was prepared in dut-ung - *E. coli*. (Kunkel, T. A. 1985). The oligonucleotide containing the desired mutation was hybridized to the UTP containing wild type M13, followed by DNA synthesis and ligation. Mutated DNA was selected for in *E. coli* 7118 cells (dut+ung+). Individual plaques were purified and evaluated for the desired mutations by restriction endonuclease digestion and dideoxynucleotide sequencing (Sequenase, USB).

7.1.6. Transfection and Isolation of Recombinant Vaccinia

HeLa cells infected with wild type vaccinia virus were transfected using the calcium phosphate method (Maniatis et al., 1982 supra, section 7.1.4.) Recombinants were isolated in TK-cells in the presence of 5-bromodeoxyuridine. Recombinant plaques were further selected for B galactosidase activity in the presence of X gal (0.2 mg/ml in PBS). After two additional plaque purifications in TK- cells, virus was amplified by infecting HeLa cells monolayers without selection. Infectivity titer was determined by plaque assay in L-2 cells.

7.1.7. Polypeptide Analysis

L-2 monolayers in 60 mm petri dishes were infected with wild type or recombinant vaccinia virus at an multiplicity of infection (moi) of 3 and were grown for 24 hours. Cells were scraped, centrifuged and lysed with 0.5% nonidet P-40. The nuclei were pelleted by centrifugation at 12,000 g for 1 minute and the cell lysate supernatant was retained. Cell lysates were run on 12% thin SDS-polyacrylamide gels. The proteins were electrophoretically transferred onto nitrocellulose and incubated with antiserum to HAV. Antibody was detected by 125I-labelled staphylococcal protein A. (Jahn, R. et al., 1984, *Proc. Natl. Acad. Sci. U.S.A.*, 81: 1684-1687).

7.1.8. Animals Studies

Six to eight week old Balb/C mice were immunized i.p. with $10^7$ pfu of either wildtype or recombinant vaccinia (rVV1 or rVV3). After 30 days a booster dose of $10$-7th pfu was administered. Mice were bled by retroorbital venous plexus puncture on day number 60.

7.1.9. Radioimmunofocus Inhibition Assay

The radioimmunofocus inhibition assay was used to detect HAV neutralizing activity in experimentally infected murine sera (Lemon and Binn, 1983, *J. Infec. Disease*, 148:1033-1039, Stapleton et al., 1985 Gastro, 89:637-642).

7.1.10. Sera

Human convalescent serum was obtained from patient D.C. following a recent infection with HAV which followed a biphastic course. Guinea pig anti-HAV serum was kindly provided by S. Feinstone, FDS, CBER). Rabbit anti-trpE/HAV VP1 serum was a gift from J. Johnston, Burroughs Wellcome).

7.2. Results

7.2.1. Construction of Plasmid and Virus Recombinants

The cloning strategy utilized the vaccinia transcriptional early/late promoter p7.5 and utilized new translation initiation sequences inserted by oligonucleotide directed mutagenesis at the start of the VP1 and VP3 coding sequences. The strategy used for VP1 and VP3 are diagrammed in FIGS. 4 and 5. An 1130 bp fragment from bp 2070-3200 containing VP1 was isolated from pHAV 1307 using Sca 1 and Hind III and subcloned into M13mp19 which had been cleaved by Hind III and Hinc II. This recombinant phage was grown in the presence of dUMP in dut-ung-*E. coli* (strain BW313) to allow for the incorporation of dUTP. A 36 nucleotide primer containing an EcoRV restriction site followed by an ATG codon at the origin of the VP1 coding sequence was kinased and annealed to the recombinant M13mp19 vector. A DNA extension reaction was performed followed by ligation. Mutated phage were selected in dut+ung+*E. coli* and dideoxynucloetide sequencing confirmed the presence of the desired mutation. This mutated recombinant M13mp19 was cleaved with EcoRV and Sma 1 and the 1000 bp fragment was ligated into the Sma 1 site of the dephosphorylated vector pSC11. Orientation of the resultant plasmid insert was confirmed by restriction mapping. The new vector pSC11-VP1 contains the early late p7.5 promoter lying immediately upstream from the new translation initiation codon placed at the beginning of the VP1 coding sequence. Thymidine kinase genes flank this construct and direct the site of homologous recombination in vaccinia virus.

Plasmid pSC11-VP3 was generated in a similar manner. A 1742 bp Bam H1 fragment of HAV spanning by 633-2375 was isolated from pHAV7. This DNA was cut with Aha II and BamHI to yield a 1058 bp fragment which was ligated with Hind II and Bam HI cut M13mp18. As with VP1, oligonucleotide directed mutagenesis was used to create a new Eco RV site followed by the ATG codon present at the origin of the VP3 coding sequence. The oligonucleotide was a 36mer spanning positions 15 to +15 with the Eco RV mutation lying 3 bp upstream of the ATG. This oligonucleotide resulted in the loss of the second methionine codon present at the origin of VP3. Additionally, a second oligonucleotide placed another Eco RV restriction site at the 3' end of VP3 resulting in a cleavage site 7 bp downstream from the VP3—VP1 cleavage site. The recombinant M13mp18 phage was sequenced and the 744 bp fragment containing the VP3 coding sequence was isolated from this double mutant using EcoRV, and was ligated to Sma 1 cut pSC11. The orientation was confirmed by restriction mapping as with pSC11-Vp1, pSC11-Vp3 contains the p7.5 promoter followed by a translation initiation codon just 5' to the origin of VP3.

The two plasmids were used to transfect HeLa cells previously infected with wild-type vaccinia virus (Reviewed in Moss and Flexner, 1987, Annual Review of Immunol., 5:305-324). Homologous recombination between vaccinia TK sequences in the plasmid and virus genome resulted in the insertion of the HAV structural genes. Recombinant vaccinia were selected by plaque assay on TK-cells in the presence of 5 bromodeoxyuridine 34 to select for TK-phenotype. Plaques were also selected for their ability to express B galactosidase activity. Indicating that the plaque is not a spontaneous TK-mutant. After two additional plaque purifications, recombinant virus stocks derived from pSCII-VP1 and pSCII-VP3 were called rVP1 and rPV3 respectively.

7.2.2. Expression of the HAV Structural Genes

Antigenic HAV VP1 and VP3 were detected by immunoblot analysis in L-2 and human B cell lines infected with rVP1 and rVP3 respectively. Human convalescent anti-HAV antisera and rabbit anti-trpE/-HAVVP1 and VP3 sera recognized a new 39,000 dalton protein (FIG. 14). The 39,000 size is larger than the expected size of VP1 which is 31,000. Our construct contains an extra 30 amino acids from the P2 region of HAV, and lies inframe with the carboxy terminal region of the flanking TK gene. Human serum recognized proteins from the rVP3 cell lysate poorly, and guinea pig anti-HAV did not recognize the rVP3 lysate.

Rabbit antisera raised against a trpE/HAV VP1 and 3 fusion protein recognized a unique band at approximately 31,000 d in the RVP3 lane from infected L-2 cells. This is the predicted size of our rVP3 construct which contains approximately 2,000 d from the frame-shifted TK gene (FIG. 15).

7.2.3. Murine Antibody Immune Response to HAV Epitopes

The ability of our vaccinia virus recombinants to elicit an antibody response to HAV was tested in mice. Three sets of three Balb/c mice were infected intraperitoneally with $10^7$ pfu of wildtype, rVP1 and rVP3. The mice were boosted on day number 30 with another intraperitoneal dose of $10^7$ pfu. On day number 60 the mice were sacrificed and serum was evaluated for their ability to recognize the vaccinia expressed HAV proteins by immunoblotting and for neutralizing activity by solid phase immunoassay. HAV VP1 and the rVP1 protein were recognized by murine sera diluted 1:50 in Western blots as did sera from mice infected with rVP3.

7.2.4. Cytotoxic T Cell Response to HAV Epitopes

CTL responses specific for the HIV-1 env glycoprotein and the nonstructural reverse transcriptase genes have been described using HIV-Vaccinia recombinants (Walker, 1988, Science, 240:64-66; Nature, 1987, 328:345). Human fibroblast cells infected with whole HAV virus do elicit a cytotoxic response in standard chromium release assays. (Vallbracht et al., Hepatology, 1986, 6:1308, J. Infect. Dis., 1989 160:209.). Our HAV vaccinia recombinant viruses can be used to study the specific epitopes involved in the cytotoxic response important to HAV infection.

8. EXAMPLE: PROCESSING OF THE RECOMBINANT HAV P1 PRECURSOR PROTEIN IN VACCINIA VIRUS AND IN BACULOVIRUS EXPRESSION SYSTEMS

The processing of the HAV P1 precursor protein into the viral capsid proteins VP4, VP2, VP3 and VP1 requires other HAV encoded proteins. In order to examine the requirements for processing the HAV P1 precursor protein, a recombinant baculovirus containing the P1 and 3C+3D (protease polymerase) coding regions under the control of independent polyhedrin promoters was constructed (FIG. 16). In addition, the 3C+3D coding region was altered by in vitro mutagenesis (3C_3D) to change the amino acid sequence at the proposed cleavage site of the protease polymerase polyprotein.

The resulting HAV expression product had six-fold higher levels of HAV antigen than the recombinant HAV baculovirus containing the HAV open reading frame described in Section 6 supra (Table 1). Human antisera that is specific to mature HAV and not denatured HAV protein recognized the HAV antigens expressed by this recombinant HAV construction. These results indicate that the 3C*D protein is capable of processing the P1 precursor protein to produce HAV.

Since the yield of HAV antigen expressed by recombinant HAV vaccinia virus is more than 50-fold higher than that expressed by recombinant HAV baculovirus (Table 1) the P1 precursor and 3C*D coding regions are presently being examined in vaccine virus vectors.

9. EXAMPLE: ISOLATION OF RECOMBINANT HEPATITIS A VIRUS CAPSIDS OR PENTAMERS

The entire Hepatitis A virus (HAV) open reading frame was cloned into vaccinia virus to obtain rVac-ORF (pHAVTF 37-27-5). Hepatitis A virus antigen was obtained from rVac-ORF infected cells and analyzed by sucrose gradients. Antigen from HAV infected cells appears in two antigenic peaks (FIG. 17). The heavier peak (on the left side of the figure) represents infectious HAV, and the middle peak at 70S represents empty capsids. In contrast, when rVac-ORF infected cell lysates were analyzed on sucrose gradients, two peaks of 70S and 15S were observed, which coincided with the HAV empty capsids and pentamers, respectively. Additionally, antigen from sucrose gradient fractions was detected by RIA using anti-HAV positive human polyclonal convalescent sera.

TABLE 1

| YIELD OF HAV ANTIGEN BY RECOMBINANT EXPRESSION SYSTEMS | |
|---|---|
| VACCINIA | |
| HAV[1] Ag/$10^7$ | Dose[2]/$10^7$ cells |
| 290 RIA std | 8 |
| (Avg. of 4 Infections) | |
| BACULOVIRUS | |
| HAV[3] Ag/$10^9$ cells | Dose[2]/$10^9$ cells |
| ORF 550 RIA std | 15 |
| (Avg. of 3 infections) | |
| P1-3CD | 90 |

[1]pHAVTF 37-27-5
[2]1 dose = 720 EU: (Weiderman et al., Vaccine 8:581, (1990))
[3]pHAVTF 34-7-1 or pHAVTF 34-7-3

Figure 18B:
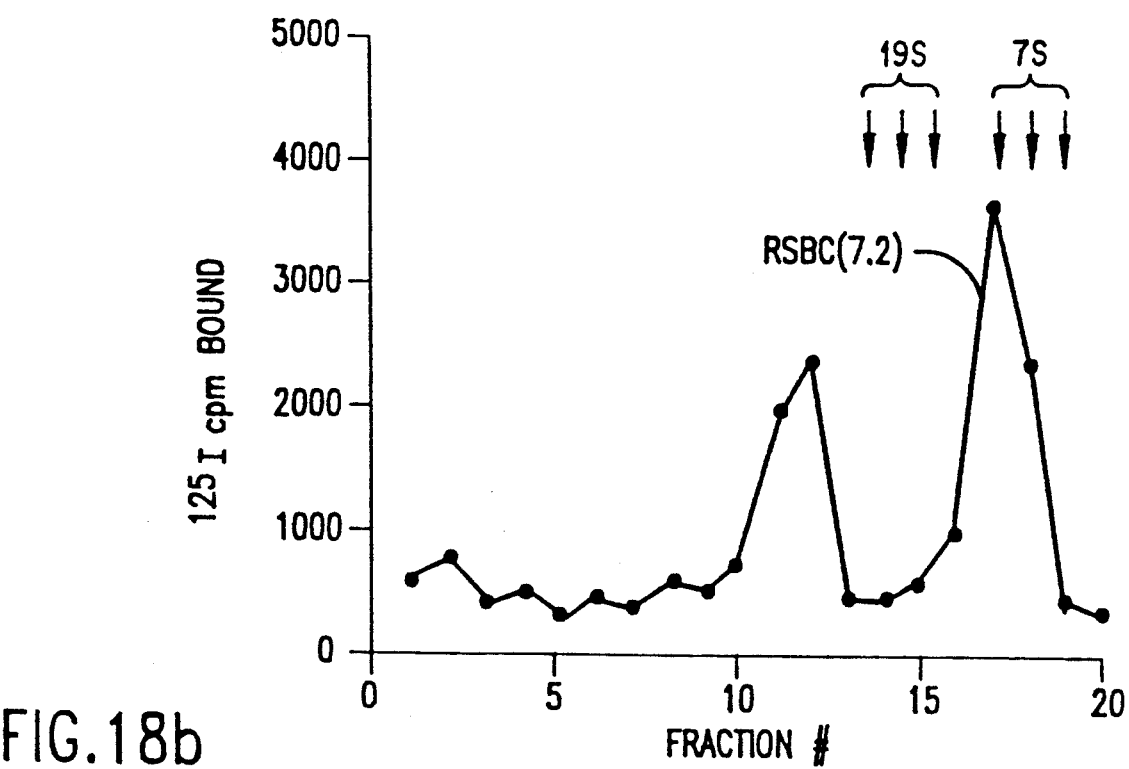

In order to maximize the amount of capsid recovered in the 70S peak, acidic pH was used in sucrose gradients of rVac-ORF infected cells. Media from rVac-ORF infected cells was removed, the cells were then suspended in either 10 mM Tris, 10 mM NaCl pH 6.5 (FIG. 18A) or 10 mM Tris, 10 mM NaCl, 50 mM Mg Cl$_2$ pH 7.2 (FIG. 18B), and then frozen at $-70°$ C. The cells were thawed and NP40 was added to a final concentration of 1%. Recombinant rVac-ORF infected cell lysates were clarified by low speed centrifugation and then analyzed on 7.5% to 45% sucrose gradients in 0.1% SDS. That data shown in FIG. 18 indicates that at pH 6.5 the HAV antigen is primarily in the form of empty capsids (FIG. 18A) while at pH 7.2 the majority of the HAV antigen is in pentamers (FIG. 18B).

10. EXAMPLE: EVALUATION OF HEPATITIS A VIRUS PARTICLES EXPRESSED BY RECOMBINANT VACCINIA VIRUSES

The hepatitis A virus (HAV) polyprotein expressed by recombinant baculoviruses and vaccinia viruses is processed into capsid proteins which assemble into virus-like particles. The recombinant HAV particles were analyzed by sucrose gradient centrifugation, immunoblotting, and solid phase radioimmunoassay employing either polyclonal human sera or monoclonal antibodies.

Both 70S (empty capsids) and 15S (pentameric) particles were present in infected cells. Immunoblots demonstrated that both particle types contained VP; (33 kDa) and a larger VP1 containing protein of 43 kDa consistent with the "PX" protein described by Anderson and Ross, *J. Virol.*, 64:5284, 1990. Radio immunoassay (RIA) of fractions collected immediately following centrifugation at 4° C. was carried out. Polyclonal anti-HAV IgG, one of four murine or one human anti-HAV monoclonal antibodies served as the capture antibody. 70S particles were recognized by all of these antibodies, but not by HAV negative control polyclonal sera or monoclonal antibody directed against non-HAV protein. Following storage at 4° C. for 5 days, fractions containing 70S particles were no longer detected by any of the 6 antibodies, suggesting that the antigenic sites were rapidly denatured.

In contrast, 15S particles were easily detected by RIA following four weeks at 4° C. These particles were bound by polyclonal human HAV antibodies, human monoclonal antibodies (K3-2F2, K24F2, B5-B3) indicating that pentamers contain these neutralization epitopes. Monoclonal antibody K3-4C8 did not bind 15S particles.

When the material from the pentamer peaks from several sucrose gradients was pooled, concentrated and analyzed on another sucrose gradient, the profile indicated the formation of an antigenic peak at 70S (FIG. 19). Thus, under these conditions, pentamers reassociate into capsids. The 70S material contained empty capsids visualized by electromicroscopy. Furthermore, this material was recognized by K3-4C8 monoclonal antibody in RIA, suggesting that the epitope was generated during assembly of pentamers into empty capsids.

11. DEPOSIT OF MICROORGANISMS

*E. coli* strain DH5 alpha carrying plasmids pHAV TF 34-7-1, pHAV TF 34-7-3, pHAV TF 37-27-5 and pHAV TF 44-23-2, which comprises either the complete or most of the HAV coding region, have been deposited with the Agricultural Research Culture Collection (NRRL), Peoria, Ill. and have been assigned accession numbers NRRL B-18636, NRRL B-18637, NRRL B-18638, and NRRL B-18813, respectively.

What is claimed is:

1. A recombinant baculovirus, the genome of which contains all coding regions of Hepatitis A Virus polyprotein controlled by regulatory elements that direct expression of the Hepatitis A Virus coding regions in a host cell infected with the recombinant baculovirus, so that the Hepatitis A Virus polyprotein is expressed and processed into pentamers or non-infectious capsid particles.

2. A recombinant vaccinia virus, the genome of which contains all coding regions of Hepatitis A Virus polyprotein controlled by regulatory elements that direct expression of the Hepatitis A Virus coding regions in a host cell infected with the recombinant vaccinia virus, so that the Hepatitis A Virus polyprotein is expressed and processed into pentamers or non-infectious capsid particles.

3. A recombinant baculovirus, the genome of which encodes the P1 precursor protein and the protease polymerase polyprotein of Hepatitis A Virus, controlled by regulatory elements that direct the expression of the Hepatitis A Virus P1 precursor protein and the protease polymerase polyprotein in a host cell infected with the recombinant baculovirus, so that the Hepatitis A Virus P1 precursor protein is expressed and processed into pentamers or non-infectious capsid particles.

4. A recombinant vaccinia virus, the genome of which encodes the P1 precursor protein and the protease polymerase polyprotein of Hepatitis A Virus, controlled by regulatory elements that direct the expression of the Hepatitis A Virus P1 precursor protein and the protease polymerase polyprotein in a host cell infected with the recombinant vaccinia virus, so that the Hepatitis A Virus P1 precursor protein is expressed and processed into pentamers or non-infectious capsid particles.

5. A composition comprising a compound selected from the group consisting of pentamers and capsids devoid of full length HAV RNA, wherein said composition is free of capsids having full length HAV RNA.

6. The recombinant vector pHAVTF 34-7-1 as deposited with the NRRL and assigned accession number B-18636.

7. The recombinant vector pHAVTF 34-7-3 as deposited with the NRRL and assigned accession number B-18637.

8. The recombinant vector pHAVTF 37-27-5 as deposited with the NRRL and assigned accession number B-18638.

9. The recombinant vector pHAVTF 44-23-2 as deposited with the NRRL and assigned accession number B-18813.

* * * * *

UNITED STATES PATENT AND TRADEMARK OFFICE
CERTIFICATE OF CORRECTION

PATENT NO.   :   5,294,548

DATED        :   March 15, 1994

INVENTOR(S)  :   James H. McLinden
                 Elliot D. Rosen
                 Particia L. Winokur
                 Jack T. Stapleton It is certified that error appears in the above-identified patent and that said Letters Patent is hereby corrected as shown below:

In the title, delete "RECOMBIANANT HEPATITIS A VIRUS" and insert in place therefore -- RECOMBINANT HEPATITIS A VIRUS VACCINE --.

Column 6, line 67, delete "vVAC-ORF" and insert in place therefore -- rVAC-ORF --.

Column 7, line 2, delete "vVac-ORF" and insert in place therefore -- rVac-ORF --.

Column 15, line 68, delete "RV-Rpnl" and insert in place therefore -- RV-Kpnl --.

Signed and Sealed this

Eleventh Day of October, 1994

Attest:

BRUCE LEHMAN

Attesting Officer        Commissioner of Patents and Trademarks